US012622878B2

(12) United States Patent
Tamagawa et al.

(10) Patent No.: US 12,622,878 B2
(45) Date of Patent: May 12, 2026

(54) CATIONIC LIPID HAVING CYSTINE SKELETON

(71) Applicants: NOF CORPORATION, Tokyo (JP); NATIONAL UNIVERSITY CORPORATION CHIBA UNIVERSITY, Chiba (JP)

(72) Inventors: Shinya Tamagawa, Kawasaki (JP); Kota Tange, Kawasaki (JP); Yuta Nakai, Kawasaki (JP); Masamichi Tamada, Kawasaki (JP); Hidetaka Akita, Chiba (JP); Hiroki Tanaka, Chiba (JP); Yu Sakurai, Chiba (JP)

(73) Assignees: NOF CORPORATION, Tokyo (JP); NATIONAL UNIVERSITY CORPORATION CHIBA UNIVERSITY, Chiba (JP)

(*) Notice: Subject to any disclaimer, the term of this patent is extended or adjusted under 35 U.S.C. 154(b) by 899 days.

(21) Appl. No.: 17/907,368

(22) PCT Filed: Mar. 19, 2021

(86) PCT No.: PCT/JP2021/011298
§ 371 (c)(1),
(2) Date: Sep. 26, 2022

(87) PCT Pub. No.: WO2021/193397
PCT Pub. Date: Sep. 30, 2021

(65) Prior Publication Data

US 2023/0127080 A1 Apr. 27, 2023

(30) Foreign Application Priority Data

Mar. 27, 2020 (JP) ................................ 2020-057383

(51) Int. Cl.
*A61K 9/51* (2006.01)
*A61K 47/54* (2017.01)
(Continued)

(52) U.S. Cl.
CPC .......... *A61K 9/5123* (2013.01); *A61K 47/543* (2017.08); *A61K 48/0033* (2013.01); *C12N 15/88* (2013.01)

(58) Field of Classification Search
CPC ................ A61K 9/5123; A61K 47/543; A61K 48/0033; A61K 47/6929; C12N 15/88; C12N 5/0012; C07C 323/58; C07C 323/59
See application file for complete search history.

(56) References Cited

U.S. PATENT DOCUMENTS

| | | | |
|---|---|---|---|
| 9,708,628 | B2 | 7/2017 | Tange et al. |
| 10,385,030 | B2 | 8/2019 | Nakai et al. |

(Continued)

FOREIGN PATENT DOCUMENTS

| | | | |
|---|---|---|---|
| EP | 2781507 | A1 | 9/2014 |
| RU | 2233834 | C2 | 8/2004 |

(Continued)

OTHER PUBLICATIONS

Hama et al., "Quantitative Comparison of Intracellular Trafficking and Nuclear Transcription between Adenoviral and Lipoplex Systems," *Mol. Ther.*, 13(4): 786-794 (2006).

(Continued)

*Primary Examiner* — Deborah D Carr
(74) *Attorney, Agent, or Firm* — Leydig, Voit & Mayer, Ltd.

(57) ABSTRACT

The present invention provides, a cationic lipid represented by the formula (1) (wherein each symbol is as defined in the
(Continued)

specification), a lipid membrane structure using the aforementioned cationic lipid, a nucleic acid-introducing agent using the aforementioned cationic lipid, and a method for introducing a nucleic acid by using the aforementioned nucleic acid-introducing agent.

(1)

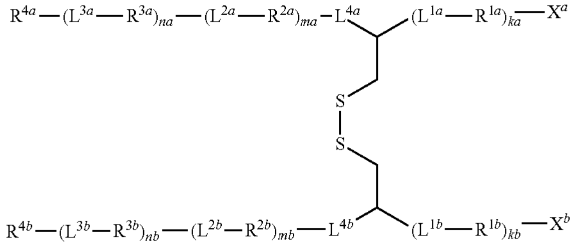

16 Claims, 2 Drawing Sheets

(51) Int. Cl.
*A61K 48/00* (2006.01)
*C12N 15/88* (2006.01)

(56) References Cited

U.S. PATENT DOCUMENTS

2014/0316006 A1 10/2014 Greaves et al.
2014/0335157 A1 11/2014 Tange et al.
2018/0155304 A1 6/2018 Nakai et al.
2018/0298379 A1 10/2018 Yang et al.
2021/0023008 A1 1/2021 Nakai et al.
2022/0192981 A1 6/2022 Nakai et al.

FOREIGN PATENT DOCUMENTS

WO WO-2012091523 A2 * 7/2012 ............ A61K 47/18
WO WO 2013/050547 A1 4/2013
WO WO 2013/073480 A1 5/2013
WO WO 2016/121942 A1 8/2016
WO WO 2019/188867 A1 10/2019

OTHER PUBLICATIONS

Jayaraman et al., "Maximizing the Potency of siRNA Lipid Nanoparticles for Hepatic Gene Silencing In Vivo," *Angew. Chem. Int. Ed. Engl.*, 51(34): 8529-8533 (2012).
Passirani et al., "Progress in Developing Cationic Systems for Non-viral Vector Systemic Gene Therapy Against Cancer," *Biomaterials.*, 29(24-25): 3477-3496 (2008).
Sato et al., "Relationship Between the Physicochemical Properties of Lipid Nanoparticles and the Quality of siRNA Delivery to Liver Cells," *Mol. Ther.*, 24(4): 788-795 (2016).
Japan Patent Office, International Search Report in International Patent Application No. PCT/JP2021/011298 (Jun. 1, 2021).
Kedika et al., "Synthesis and Gene Transfer Activities of Novel Serum Compatible Reducible Tocopherol-Based Cationic Lipids," *Mol. Pharm.*, 9(5): 1146-1162 (2012).
Ma et al., "The Role of Disulfide-bridge on the Activities of H-shape Gemini-like Cationic Lipid Based siRNA Delivery," *J. Control. Release*, 235: 99-111 (2016).
Zhang et al., "Cationic Gemini Lipids with Cyclen Headgroups: Interaction with DNA and Gene Delivery Abilities," *RSC Adv.*, 4: 44261-44268 (2014).

* cited by examiner

CATIONIC LIPID HAVING CYSTINE SKELETON

TECHNICAL FIELD

The present invention relates to a cationic lipid having a cystine skeleton, a lipid membrane structure containing the same, and use thereof.

BACKGROUND ART

For practicalization of nucleic acid therapy, an effective and safe nucleic acid delivery carrier is demanded. While virus vectors are nucleic acid delivery carriers with good expression efficiency, the development of non-viral nucleic acid delivery carriers that can be used more safely is ongoing. Among them, carriers using a cationic lipid are non-viral nucleic acid delivery carriers most generally used at present.

Cationic lipids are largely composed of an amine moiety and a lipid moiety, wherein the amine moiety showing cationicity and a polyanion nucleic acid electrostatically interact to form a liposome or lipid membrane structure, which promotes uptake into cells and delivers the nucleic acid into cells.

As known cationic lipids generally and widely used, DOTAP and DODAP can be mentioned. These known cationic lipids form a positively-charged liposome or lipid membrane structure when combined with a phospholipid, which electrostatically interacts with a nucleic acid to be able to deliver the nucleic acid to the target cells (non-Patent Literature 1).

On the other hand for a lipid membrane structure using a cationic lipid to exhibit a practical effect in vivo as a nucleic acid delivery carrier, the requirements of good pharmacokinetics, specifically high stability in blood, property to highly accumulate in the target tissues such as liver, tumor, and the like need to be fulfilled. In response to this problem, the following report on examples of improving pharmacokinetics by adjusting surface pKa of lipid membrane structures.

Non-Patent Literature 2 and non-Patent Literature 3 show that pharmacokinetics and distribution in each cell in the liver can be controlled by adjusting the surface pKa of lipid membrane structures. Furthermore, these literatures describe that escape of lipid membrane structures from endosomes is promoted and nucleic acids can be efficiently delivered into the cytoplasm by adjusting the pKa of lipid membrane structures to a value advantageous for endosome escape.

While cationic lipids having improved pharmacokinetics have been developed as shown above, in view of the property of the nucleic acid delivery carriers that they generally introduce exogenous substances into cells, a large effect output from a small uptake amount is desired. That is, when a lipid membrane structure is used as a delivery carrier of an expression vector into cells, it is desired to increase the expression level per unit lipid membrane structure incorporated into the cells and enhance intracellular expression efficiency. To enhance the intracellular expression efficiency, it is necessary to also improve, besides pharmacokinetics, intracellular kinetics such as uptake process into cells, escape from endosome, nuclear membrane permeation, and the like (non-Patent Literature 4).

There are examples in which intracellular dynamics were improved by imparting biodegradability to cationic lipids (Patent Literatures 1 to 4). These literatures describe a cationic lipid having a structure linked by a biodegradable disulfide bond. These literatures show that the cationic lipid can improve intracellular dynamics by dissociating nucleic acid from a lipid membrane structure by utilizing intracellular cleavage of a disulfide bond. In fact, it has been clarified that the cationic lipid can improve intracellular dynamics such as improvement of delivery efficiency of nucleic acid into the cytoplasm and the like, since it shows high nucleic acid delivery efficiency as compared with known cationic lipids, DOTAP and DODAP. Furthermore, the effect of reducing toxicity is expected by imparting degradability.

As shown above, there are plural reports on improving the pharmacokinetics and intracellular dynamics of nucleic acid delivery carriers by adjusting the surface pKa of lipid membrane structures, introducing disulfide bonds with degradability, and the like. However, nucleic acid therapy targets a wide variety of diseases. In order to establish a treatment method suitable for each disease, it is desired to increase the lipid types available for selection and further improve the effect.

CITATION LIST

Patent Literature

[PTL 1]
U.S. Pat. No. 9,708,628
[PTL 2]
WO 2016/121942
[PTL 3]
WO 2019/188867

PTL 4

US 2018/0298379
Non Patent Literature
[NPL 1]
Biomaterials 29(24-25): 3477-96, 2008
[NPL 2]
Molecular Therapy 24(4): 788-795, 2016
[NPL 3]
Angewante Chemie International Edition 51: 8529-8533, 2012
[NPL 4]
Molecular Therapy 13(4): 786-794, 2006

SUMMARY OF INVENTION

Technical Problem

The problem of the present invention is to provide a cationic lipid that shows good intracellular dynamics and can be used as a carrier for nucleic acid delivery, a lipid membrane structure using the aforementioned cationic lipid, a nucleic acid-introducing agent using the aforementioned cationic lipid, and a method for introducing a nucleic acid by using the aforementioned nucleic acid-introducing agent.

Solution to Problem

In view of the above-mentioned problems, the present inventors have conducted intensive studies and found a cationic lipid that can adjust surface pKa of a lipid membrane structure and can improve pharmacokinetics and intracellular dynamics. Specifically, the cationic lipid has a cystine skeleton into which a lipid moiety and an amine moiety have been introduced. Since the cationic lipid has a disulfide bond, the disulfide bond is cleaved in cells, thus also affording an effect of dissociating a nucleic acid from a lipid membrane structure. They have found that a lipid membrane structure containing the novel cationic lipid can deliver nucleic acid efficiently into the cytoplasm.

Accordingly, the present invention includes the following.

[1] A cationic lipid represented by the formula (1):

(1)

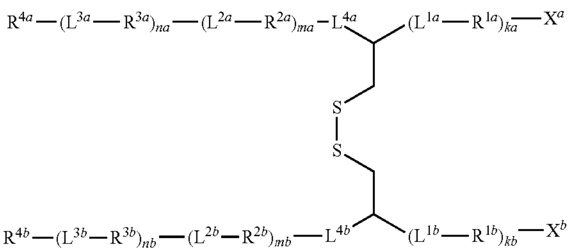

wherein $L^{1a}$ and $L^{1b}$ are each independently an amide bond, a carbamate bond, or a urea bond, $R^{1a}$ and $R^{1b}$ are each independently an alkylene group having not more than 8 carbon atoms or an oxydialkylene group having not more than 8 carbon atoms, ka and kb are each independently 0 or 1, $X^a$ and $X^b$ are each independently a dialkylamino group (the aforementioned two alkyl groups each independently have 1 to 5 carbon atoms), or a 3- to 6-membered cyclic amino group, $L^{4a}$ and $L^{4b}$ are each independently an ester bond or an amide bond, $R^{2a}$ and $R^{2b}$ are each independently an alkylene group having not more than 8 carbon atoms or an oxydialkylene group having not more than 8 carbon atoms, $L^{2a}$ and $L^{2b}$ are each independently an ester bond, an amide bond, a carbamate bond, an ether bond, or a urea bond, ma and mb are each independently 0 or 1, $R^{3a}$ and $R^{3b}$ are each independently a divalent group derived from an aromatic compound having 3 to 16 carbon atoms and at least one aromatic ring, and optionally having a hetero atom, $L^{3a}$ and $L^{3b}$ are each independently an ester bond, an amide bond, a carbamate bond, an ether bond, or a urea bond, na and nb are each independently 0 or 1, $R^{4a}$ and $R^{4b}$ are each independently an aliphatic hydrocarbon group having 12 to 22 carbon atoms, or $R^5$—CO—$(CH_2)_p$—, $R^5$ is a residue of a liposoluble vitamin having a hydroxy group or a residue of a sterol derivative having a hydroxy group, and p is 2 or 3.

[2] The cationic lipid of the aforementioned [1], wherein the na and nb are both 1.

[3] The cationic lipid of the aforementioned [1] or [2], wherein the $R^{3a}$ and $R^{3b}$ are each independently a group represented by the formula (2):

(2)

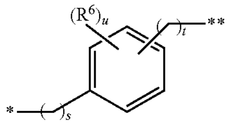

wherein

* shows a bonding position with $L^{3a}$ or $L^{3b}$,

** shows a bonding position with $L^{2a}$, $L^{2b}$, $L^{4a}$, or $L^{4b}$, s is an integer of 0 to 3, t is an integer of 0 to 3, u is an integer of 0 to 4, and $R^6$ in the number of u are each independently a substituent.

[4] The cationic lipid of the aforementioned [3], wherein the s is 0.

[5] The cationic lipid of any one of the aforementioned [1] to [4], wherein the ka and kb are both 0.

[6] The cationic lipid of any one of the aforementioned [1] to [4], wherein the ka and kb are both 1.

[7] The cationic lipid of any one of the aforementioned [1] to [6], wherein the $R^5$ is a residue of a liposoluble vitamin having a hydroxy group.

[8] The cationic lipid of any one of the aforementioned [1] to [6], wherein the $R^{4a}$ and $R^{4b}$ are each independently an aliphatic hydrocarbon group having 12 to 22 carbon atoms.

[9] The cationic lipid of any one of the aforementioned [1] to [6], wherein the $R^{4a}$ and $R^{4b}$ are each independently $R^5$—CO—$(CH_2)_p$—, and $R^5$ is a residue of a liposoluble vitamin having a hydroxy group.

[10] A lipid membrane structure comprising the cationic lipid of any one of the aforementioned [1] to [9] as a constituent lipid of the membrane.

[11] A nucleic acid-introducing agent comprising the cationic lipid of any one of the aforementioned [1] to [9], or the lipid membrane structure of the aforementioned [10].

[12] A method for introducing a nucleic acid into a cell in vitro, comprising bringing the nucleic acid-introducing agent of the aforementioned [11] into contact with the cell, wherein the nucleic acid is encapsulated in the nucleic acid-introducing agent.

[13] A method for introducing a nucleic acid into a target cell, comprising administering the nucleic acid-introducing agent of the aforementioned [11] to a living organism to allow for delivery of the nucleic acid to the cell, wherein the nucleic acid is encapsulated in the nucleic acid-introducing agent.

Advantageous Effects of Invention

The present invention relates to a cationic lipid having a biodegradable cystine skeleton into which a dialkylamino group or a cyclic amino group, and a lipid moiety have been introduced, a lipid membrane structure containing the cationic lipid, and use of these. The cationic lipid of the present invention can form a lipid membrane structure. The cationic lipid and the lipid membrane structure of the present invention can be used for a nucleic acid-introducing agent. The cationic lipid of the present invention can adjust pKa widely by positioning the amine moiety at the end of the molecular structure, allowing for structural change near the amine moiety. Furthermore, the disulfide bond contained in the cystine skeleton of the cationic lipid of the present invention is cleaved in the intracellular reductive environment, thus promoting release of materials (nucleic acid) enclosed therein. Hence, a nucleic acid-introducing agent using the cationic lipid of the present invention can achieve high efficiency of nucleic acid delivery into the cytoplasm.

When nucleic acid is introduced using the cationic lipid of the present invention, or a lipid membrane structure containing the same, degradation of the nucleic acid by the serum components is suppressed, which is advantageous for nucleic acid introduction in the presence of serum or nucleic acid introduction in vivo.

DESCRIPTION OF EMBODIMENTS

Figure 1:
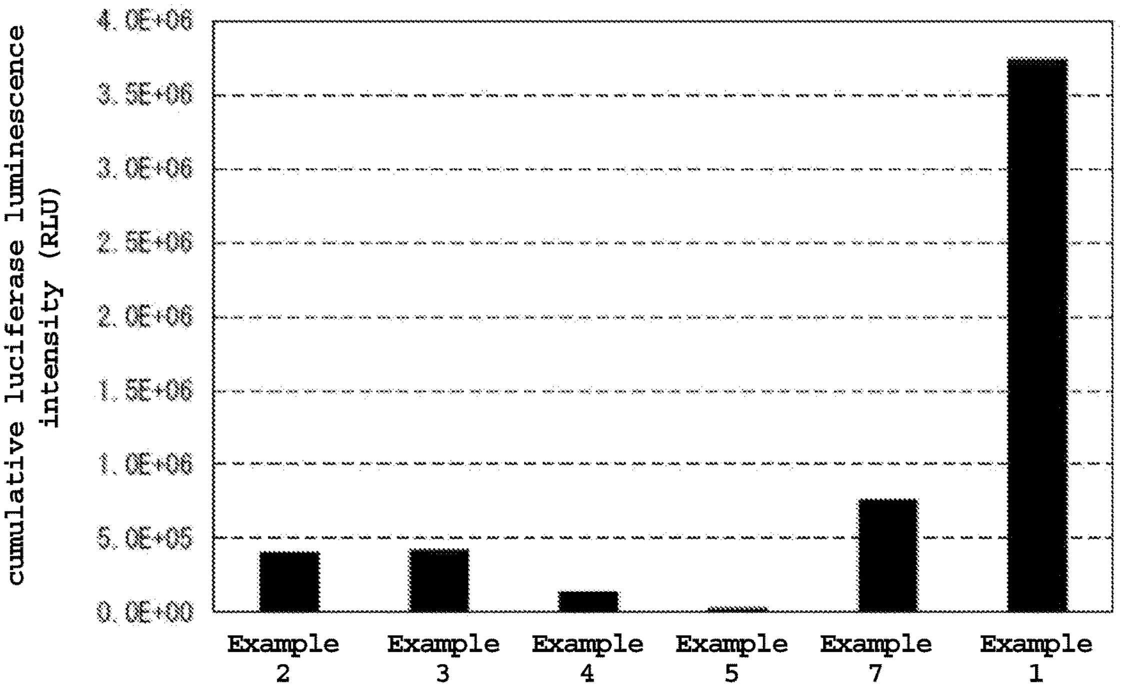
FIG. 1 shows in vitro gene expression activity in Jurkat cells of various lipid nano particles (sometimes to be abbreviated as "LNP" in the present specification) prepared from the cationic lipid of the present invention.

While the embodiments of the present invention are described in the following, the present invention is not limited thereto.

The present invention provides a cationic lipid represented by the formula (1):

(1)

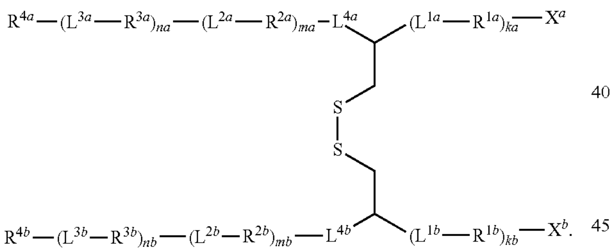

Only one kind of the aforementioned cationic lipid may be used, or two or more kinds thereof may be used in combination. In the following, the "cationic lipid represented by the formula (1)" is sometimes to be abbreviated as "cationic lipid (1)". The compounds and the like represented by other formulas may also be abbreviated in the same manner sometimes.

$L^{1a}$ and $L^{1b}$ are each independently an amide bond, a carbamate bond, or a urea bond, preferably each independently an amide bond or a carbamate bond, more preferably both amide bonds.

$L^{1a}$ and $L^{1b}$ may be the same or different, and $L^{1a}$ and $L^{1b}$ are preferably the same.

$L^{1a}$ and $L^{1b}$ are preferably each independently *—NH—CO—**, *—NH—CO—O—**, or *—NH—CO—NH—**, more preferably each independently *—NH—CO—** or *—NH—CO—O—**, more preferably both *—NH—CO— (in the aforementioned formulas,  indicates a bonding position with $R^{1a}$ or $R^{1b}$, and * indicates a bonding position with a carbon atom on the opposite side from $R^{1a}$ or $R^{1b}$). As used herein, the "bonding position with $R^{1a}$ or $R^{1b}$" means "bonding position with $R^{1a}$" for $L^{1a}$ and the "bonding position with $R^{1b}$" for $L^{1b}$. In addition, the "bonding position with a carbon atom on the opposite side from $R^{1a}$ or $R^{1b}$" means a "bonding position with a carbon atom on the opposite side from $R^{1a}$" for $L^{1a}$, and a "bonding position with a carbon atom on the opposite side from $R^{1b}$" for $L^{1b}$. Other similar indications mean the same.

$R^{1a}$ and $R^{1b}$ are each independently an alkylene group having not more than 8 carbon atoms or an oxydialkylene group having not more than 8 carbon atoms, preferably each independently an alkylene group having not more than 8 carbon atoms. $R^{1a}$ and $R^{1b}$ may be the same or different, and $R^{1a}$ and $R^{1b}$ are preferably the same.

The alkylene group having not more than 8 carbon atoms for $R^{1a}$ or $R^{1b}$ may be linear or branched, and is preferably linear. The number of carbon atoms contained in the aforementioned alkylene group is preferably not more than 6, more preferably not more than 4.

Examples of the alkylene group having not more than 8 carbon atoms for $R^{1a}$ or $R^{1b}$ include methylene group, ethylene group, trimethylene group, isopropylene group ($—CH(CH_3)CH_2—$, $—CH_2CH(CH_3)—$), tetramethylene group, isobutylene group ($—C(CH_3)_2CH_2—$, $—CH_2C(CH_3)_2—$), pentamethylene group, hexamethylene group, heptamethylene group, octamethylene group, and the like.

The alkylene group having not more than 8 carbon atoms for $R^{1a}$ or $R^{1b}$ is preferably a methylene group, an ethylene group, a trimethylene group, a tetramethylene group, an isopropylene group ($—CH(CH_3)CH_2—$, $—CH_2CH(CH_3)—$), an isobutylene group ($—C(CH_3)_2CH_2—$, $—CH_2C(CH_3)_2—$), a pentamethylene group, or a hexamethylene group, more preferably a methylene group, an ethylene group, a trimethylene group, an isopropylene group ($—CH(CH_3)CH_2—$, $—CH_2CH(CH_3)—$), a tetramethylene group, or an isobutylene group ($—C(CH_3)_2CH_2—$, $—CH_2C(CH_3)_2—$).

The oxydialkylene group having not more than 8 carbon atoms means a divalent group having a structure in which two alkylene groups are bonded via an oxy group (—O—) (i.e., alkylene-O-alkylene), wherein the total of the carbon atoms of the two alkylene groups is not more than 8. As used herein, the two alkylene groups may be the same or different, preferably the same.

Examples of the oxydialkylene group having not more than 8 carbon atoms for $R^{1a}$ or $R^{1b}$ include oxydimethylene group (methyleneoxymethylene group), oxydiethylene group (ethyleneoxyethylene group), oxydi(trimethylene) group (trimethylene oxytrimethylene group), and oxydibutylene group (butyleneoxybutylene group). The oxydialkylene group having not more than 8 carbon atoms is preferably an oxydimethylene group (methyleneoxymethylene group), an oxydiethylene group (ethyleneoxyethylene group), or an oxydi(trimethylene) group (trimethylene oxytrimethylene group), more preferably an (ethyleneoxyethylene group).

$R^{2a}$ and $R^{2b}$ are preferably each independently an alkylene group having not more than 8 carbon atoms, more preferably each independently a methylene group, an ethylene group, a trimethylene group, a tetramethylene group, an isopropylene group ($—CH(CH_3)CH_2—$, $—CH_2CH(CH_3)—$), an isobutylene group ($—C(CH_3)_2CH_2—$, $—CH_2C(CH_3)_2—$), a pentamethylene group, or a hexamethylene group, further preferably each independently a methylene group, an ethylene group, a trimethylene group, an isopropylene group ($—CH(CH_3)CH_2—$, $—CH_2CH(CH_3)—$), a tetramethylene group, or an isobutylene group (—$C(CH_3)_2CH_2$—, —$CH_2C(CH_3)_2$—), particularly preferably both methylene groups.

ka and kb are each independently 0 or 1. As used herein, ka of 0 means absence of $L^{1a}$-$R^{1a}$. kb and the like being 0 means the same. ka and kb are preferably both 1.

A cationic lipid (1) wherein ka and kb are both 0 is represented by the following formula (1a):

(1a)

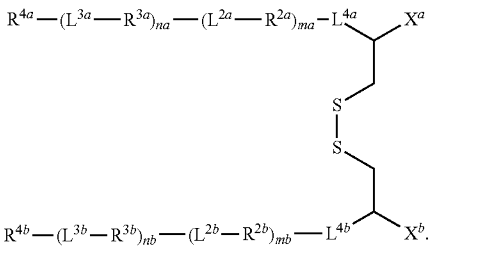

A cationic lipid (1) wherein ka and kb are both 1 is represented by the following formula (1b):

(1b)

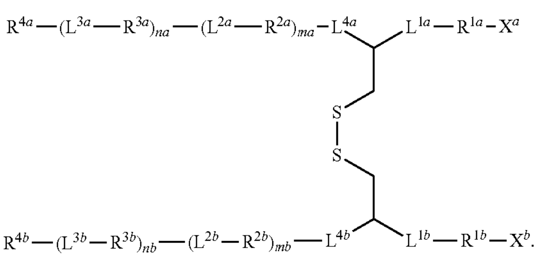

$X^a$ and $X^b$ are each independently a dialkylamino group (the aforementioned two alkyl groups each independently have 1 to 5 carbon atoms), or a 3- to 6-membered cyclic amino group. $X^a$ and $X^b$ may be the same or different, and $X^a$ and $X^b$ are preferably the same.

The carbon numbers of the two alkyl groups in the dialkylamino group are preferably each independently 1 to 3, more preferably both 1. The total of the carbon numbers of the two alkyl groups in the dialkylamino group is preferably 2 to 6, more preferably 2 to 4.

Examples of the alkyl group in the dialkylamino group include methyl group, ethyl group, propyl group, isopropyl group, cyclopropyl group, n-butyl group, sec-butyl group, isobutyl group, tert-butyl group, cyclobutyl group, pentyl group, isopentyl group, neopentyl group, tert-pentyl group, 1,2-dimethylpropyl group, 2-methylbutyl group, cyclopentyl group, and the like. The two alkyl groups in the dialkylamino group are preferably each independently a methyl group, an ethyl group, a propyl group, or an isopropyl group, more preferably both methyl groups.

The 3- to 6-membered cyclic amino group means a group in which the substituents of the amino group are bonded to form a ring, and the number of atoms forming the aforementioned ring is 3 to 6. The 3- to 6-membered cyclic amino group is preferably a 5- or 6-membered cyclic amino group, more preferably a 6-membered cyclic amino group. As the cyclic amino group, an amino group in which the ring is formed from a nitrogen atom and a methylene group (—$CH_2$—) alone is preferred.

Examples of the 3- to 6-membered cyclic amino group include 1-aziridinyl group, 1-azetidinyl group, 1-pyrrolidinyl group, 1-piperidyl group, 4-morpholinyl group, 4-thiomorpholinyl group, and the like. The 3- to 6-membered cyclic amino group is preferably a 1-pyrrolidinyl group or a 1-piperidyl group, more preferably a 1-piperidyl group.

$X^a$ and $X^b$ are preferably each independently a dialkylamino group (the aforementioned two alkyl groups each independently have 1 to 3 carbon atoms), or a 5- or 6-membered cyclic amino group, more preferably each independently a dimethylamino group, an N-methyl-N-ethylamino group, an N-methyl-N-propylamino group, a diethylamino group, a dipropylamino group, a di(isopropyl)amino group, or a 1-piperidyl group. $X^a$ and $X^b$ are further preferably the same and each is a dimethylamino group, an N-methyl-N-ethylamino group, an N-methyl-N-propylamino group, a diethylamino group, a dipropylamino group, a di(isopropyl)amino group, or a 1-piperidyl group. $X^a$ and $X^b$ are particularly preferably both dimethylamino groups.

$L^{4a}$ and $L^{4b}$ are each independently an ester bond or an amide bond, preferably both ester bonds.

$L^{4a}$ and $L^{4b}$ may be the same or different, and $L^{4a}$ and $L^{4b}$ are preferably the same.

$L^4$ and $L^{4b}$ are preferably each independently *—O—CO—** or *—NH—CO—**, more preferably both *—O—CO—** (in the aforementioned formulas, * indicates a bonding position with $R^{2a}$, $R^{2b}$, $R^{3a}$, $R^{3b}$, $R^{4a}$, or $R^{4b}$, and ** indicates a bonding position with a carbon atom on the opposite side from $R^{2a}$, $R^{2b}$, $R^{3a}$, $R^{3b}$, $R^{4a}$, or $R^{4b}$). As used herein, the "bonding position with $R^{2a}$, $R^{2b}$, $R^{3a}$, $R^{3b}$, $R^{4a}$, or $R^{4b}$" means a bonding position with $R^{2a}$ for $L^{4a}$ when ma is 1 (i.e., $L^{2a}$-$R^{2a}$ is present), means a bonding position with $R^{3a}$ for $L^{4a}$ when ma is 0 (i.e., $L^{2a}$-$R^{2a}$ is absent) and na is 1 (i.e., $L^{3a}$-$R^{3a}$ is present), and means a bonding position with $R^4$ for $L^4$ when ma is 0 (i.e., $L^{2a}$-$R^{2a}$ is absent) and na is 0 (i.e., $L^{3a}$-$R^{3a}$ is absent). Other similar indications mean the same.

$R^{2a}$ and $R^{2b}$ are each independently an alkylene group having not more than 8 carbon atoms or an oxydialkylene group having not more than 8 carbon atoms. $R^{2a}$ and $R^{2b}$ may be the same or different, and $R^{2a}$ and $R^{2b}$ are preferably the same.

The alkylene group having not more than 8 carbon atoms for $R^{2a}$ or $R^{2b}$ may be linear or branched, and is preferably linear. The number of carbons contained in the aforementioned alkylene group is preferably not more than 6, more preferably not more than 4.

Examples of the alkylene group having not more than 8 carbon atoms for $R^{2a}$ or $R^{2b}$ include methylene group, ethylene group, trimethylene group, isopropylene group (—$CH(CH_3)CH_2$—, —$CH_2CH(CH_3)$—), tetramethylene group, isobutylene group (—$C(CH_3)_2CH_2$—, —$CH_2C(CH_3)_2$—), pentamethylene group, hexamethylene group, heptamethylene group, octamethylene group, and the like.

The alkylene group having not more than 8 carbon atoms for $R^{2a}$ or $R^{2b}$ is preferably a methylene group, an ethylene group, a trimethylene group, a tetramethylene group, an isobutylene group (—$C(CH_3)_2CH_2$—, —$CH_2C(CH_3)_2$—), a pentamethylene group, or a hexamethylene group, more preferably an ethylene group, a trimethylene group, a tetramethylene group, or an isobutylene group (—$C(CH_3)_2CH_2$—, —$CH_2C(CH_3)_2$—), further preferably an ethylene group.

The two alkylenes present in the oxydialkylene group having not more than 8 carbon atoms for $R^{2a}$ or $R^{2b}$ may be the same as or different from each other, and preferably the same.

Examples of the oxydialkylene group having not more than 8 carbon atoms for $R^{2a}$ or $R^{2b}$ include oxydimethylene group (methyleneoxymethylene group), oxydiethylene group (ethyleneoxyethylene group), oxydi(trimethylene) group (trimethylene oxytrimethylene group), oxydibutylene group, and the like.

The oxydialkylene group having not more than 8 carbon atoms for $R^{2a}$ or $R^{2b}$ is preferably an oxydimethylene group (methyleneoxymethylene group), an oxydiethylene group (ethyleneoxyethylene group), or an oxydi(trimethylene) group (trimethylene oxytrimethylene group), more preferably an oxydiethylene group (ethyleneoxyethylene group).

$R^{2a}$ and $R^{2b}$ are preferably each independently an alkylene group having not more than 8 carbon atoms, more preferably each independently a methylene group, an ethylene group, a trimethylene group, a tetramethylene group, an isobutylene group ($—C(CH_3)_2CH_2—$, $—CH_2C(CH_3)_2—$), a pentamethylene group, or a hexamethylene group, further preferably each independently an ethylene group, a trimethylene group, a tetramethylene group, or an isobutylene group ($—C(CH_3)_2CH_2—$, $—CH_2C(CH_3)_2—$), particularly preferably both ethylene groups.

$L^{2a}$ and $L^{2b}$ are each independently an ester bond, an amide bond, a carbamate bond, an ether bond, or a urea bond, preferably each independently an ester bond, an amide bond, or a carbamate bond, more preferably both ester bonds.

$L^{2a}$ and $L^{2b}$ may be the same or different, and $L^{2a}$ and $L^{2b}$ are preferably the same.

$L^{2a}$ and $L^{2b}$ are preferably each independently *—CO—O—**, *—O—CO—**, *—CO—NH—**, *—NH—CO—**, *—NH—CO—O—**, *—O—CO—NH—**, *—O—**, or *—NH—CO—NH—**, more preferably each independently *—CO—O—**, *—CO—NH—**, or *—NH—CO—O—**, further preferably both *—CO—O—** (in the aforementioned formulas, * indicates a bonding position with $R^{3a}$, $R^{3b}$, $R^{4a}$, or $R^{4b}$, and ** indicates a bonding position with $R^{2a}$ or $R^{2b}$)

The ma and mb are each independently 0 or 1, preferably both 1.

A cationic lipid (1) wherein ma and mb are both 0 is represented by the following formula (1c):

(1c)

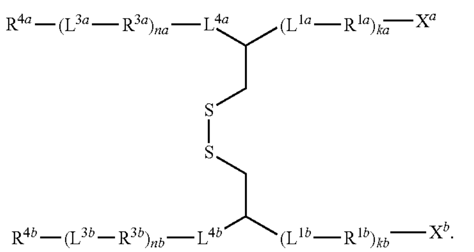

A cationic lipid (1) wherein ma and mb are both 1 is represented by the following formula:

(1d)

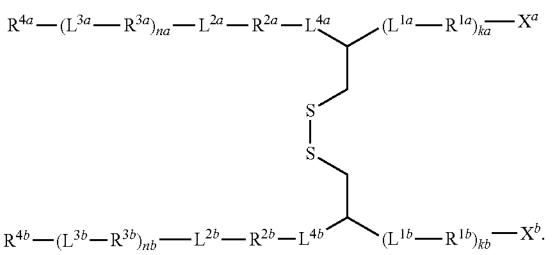

$R^{3a}$ and $R^{3b}$ are each independently a divalent group derived from an aromatic compound having 3 to 16 carbon atoms and at least one aromatic ring, and optionally having a hetero atom. As used herein, the aforementioned divalent group means a divalent group having a structure obtained by removing two hydrogen atoms from the aforementioned aromatic compound. The number of carbons contained in the aforementioned aromatic compound is preferably 6 to 12, more preferably 6 or 7. The number of aromatic ring contained in the aforementioned aromatic compound is preferably 1. $R^{3a}$ and $R^{3b}$ may be the same or different, and $R^{3a}$ and $R^{3b}$ are preferably the same.

The aromatic ring of the aforementioned aromatic compound may be an aromatic hydrocarbocycle or an aromatic heterocycle. Examples of the aromatic hydrocarbocycle include benzene ring, naphthalene ring, anthracene ring, and the like. Examples of the aromatic heterocycle include imidazole ring, pyrazole ring, oxazole ring, isoxazole ring, thiazole ring, isothiazole ring, triazine ring, pyrrole ring, furanthiophene ring, pyrimidine ring, pyridazine ring, pyrazine ring, pyridine ring, purine ring, pteridine ring, benzimidazole ring, indole ring, benzofuran ring, quinazoline ring, phthalazine ring, quinoline ring, isoquinoline ring, coumarin ring, chromone ring, benzodiazepine ring, phenoxathiine ring, phenothiazine ring, acridine ring, and the like. The aromatic ring of the aforementioned aromatic compound is preferably a benzene ring, a naphthalene ring, or a anthracene ring, more preferably a benzene ring.

The aromatic ring of the aforementioned aromatic compound may have a substituent. Examples of the aforementioned substituent include acyl group having 2 to 4 carbon atoms, alkoxycarbonyl group having 2 to 4 carbon atoms, carbamoyl group having 2 to 4 carbon atoms, acyloxy group having 2 to 4 carbon atoms, acylamino group having 2 to 4 carbon atoms, alkoxycarbonylamino group having 2 to 4 carbon atoms, fluorine atom, chlorine atom, bromine atom, iodine atom, alkylsulfanyl group having 1 to 4 carbon atoms, alkylsulfonyl group having 1 to 4 carbon atoms, arylsulfonyl group having 6 to 10 carbon atoms, nitro group, trifluoromethyl group, cyano group, alkyl group having 1 to 4 carbon atoms, ureido group having 1 to 4 carbon atoms, alkoxy group having 1 to 4 carbon atoms, aryl group having 6 to 10 carbon atoms, aryloxy group having 6 to 10 carbon atoms, and the like. Preferable examples of the aforementioned substituent include acetyl group, methoxycarbonyl group, methylcarbamoyl group, acetoxy group, acetamido group, methoxycarbonylamino group, fluorine atom, chlorine atom, bromine atom, iodine atom, methylsulfanyl group, phenylsulfonyl group, nitro group, trifluoromethyl group, cyano group, methyl group, ethyl group, propyl group, isopropyl group, tert-butyl group, ureido group, methoxy group, ethoxy group, propoxy group, isopropoxy group, tert-butoxy group, phenyl group, phenoxy group, and the like.

$R^{3a}$ and $R^{3b}$ are preferably each independently a group represented by the formula (2):

(2)

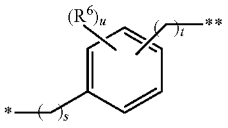

wherein

* indicates a bonding position with $L^{3a}$ or $L^{b}$,

** indicates a bonding position with $L^{2a}$, $L^{2b}$ $L^{4a}$, or $L^{4b}$ s is an integer of 0 to 3, t is an integer of 0 to 3, u is an integer of 0 to 4, and $R^6$ in the number of u are each independently a substituent.

The s is preferably 0 or 1, more preferably 0.

The t is preferably an integer of 0 to 2, more preferably 1.

The u is preferably an integer of 0 to 2, more preferably 0 or 1, further preferably 0.

Examples of the $R^6$ include acyl group having 2 to 4 carbon atoms, alkoxycarbonyl group having 2 to 4 carbon atoms, carbamoyl group having 2 to 4 carbon atoms, acyloxy group having 2 to 4 carbon atoms, acylamino group having 2 to 4 carbon atoms, alkoxycarbonylamino group having 2 to 4 carbon atoms, fluorine atom, chlorine atom, bromine atom, iodine atom, alkylsulfanyl group having 1 to 4 carbon atoms, alkylsulfonyl group having 1 to 4 carbon atoms, arylsulfonyl group having 6 to 10 carbon atoms, nitro group, trifluoromethyl group, cyano group, alkyl group having 1 to 4 carbon atoms, ureido group having 1 to 4 carbon atoms, alkoxy group having 1 to 4 carbon atoms, aryl group having 6 to 10 carbon atoms, aryloxy group having 6 to 10 carbon atoms, and the like. Preferable examples of the $R^6$ include acetyl group, methoxycarbonyl group, methylcarbamoyl group, acetoxy group, acetamido group, methoxycarbonylamino group, fluorine atom, chlorine atom, bromine atom, iodine atom, methylsulfanyl group, phenylsulfonyl group, nitro group, trifluoromethyl group, cyano group, methyl group, ethyl group, propyl group, isopropyl group, tert-butyl group, ureido group, methoxy group, ethoxy group, propoxy group, isopropoxy group, tert-butoxy group, phenyl group, phenoxy group, and the like. When $R^6$ is present in plurality, plural $R^6$ may be the same or different.

$L^{3a}$ and $L^{3b}$ are each independently an ester bond, an amide bond, a carbamate bond, an ether bond, or a urea bond, are preferably each independently an ester bond, an amide bond, or an ether bond, more preferably both are ester bonds.

$L^{3a}$ and $L^{3b}$ may be the same or different, and $L^{3a}$ and $L^{3b}$ are preferably the same groups.

$L^{3a}$ and $L^{3b}$ are preferably each independently *—CO—O—**, *—O—CO—**, *—CO—NH—**, *—NH—CO—**, *—NH—CO—O—**, *—O—CO—NH—**, *—O—**, or *—NH—CO—NH—**, more preferably each independently *—CO—O—**, *—CO—NH—**, or *—NH—CO—O—**, further preferably both *—CO—O—** (in the aforementioned formulas, * indicates a bonding position with $R^{4a}$ or $R^{4b}$, and ** indicates a bonding position with $R^{3a}$ or $R^{3b}$).

The na and nb are each independently 0 or 1, preferably both 1.

A cationic lipid (1) wherein na and nb are both 0 is represented by the following formula (1e):

(1e)

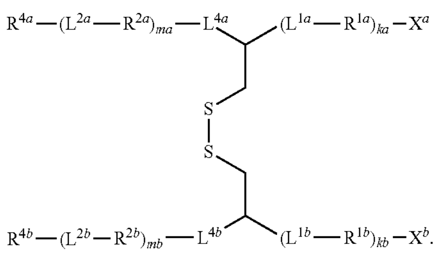

A cationic lipid (1) wherein na and nb are both 1 is represented by the following formula (1f):

(1f)

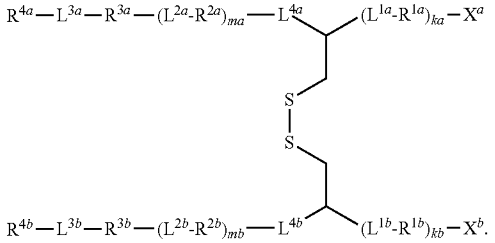

$R^{4a}$ and $R^{4b}$ are each independently an aliphatic hydrocarbon group having 12 to 22 carbon atoms or $R^5$—CO—$(CH_2)_p$—, $R^5$ is a residue of a liposoluble vitamin having a hydroxy group or a residue of a sterol derivative having a hydroxy group, and p is 2 or 3. $R^{4a}$ and $R^{4b}$ may be the same or different, and $R^{4a}$ and $R^{4b}$ are preferably the same groups.

In the present specification, the residue of a liposoluble vitamin having a hydroxy group refers to a monovalent group having a structure obtained by removing a hydrogen atom from the hydroxy group of the aforementioned liposoluble vitamin. In addition, the residue of a sterol derivative having a hydroxy group refers to a monovalent group having a structure obtained by removing a hydrogen atom from the hydroxy group of the aforementioned sterol derivative.

The aliphatic hydrocarbon group having 12 to 22 carbon atoms may be linear or branched. The number of carbons contained in the aforementioned aliphatic hydrocarbon group is preferably 13 to 19, more preferably 13 to 17.

The aforementioned aliphatic hydrocarbon group may be saturated or unsaturated. In the case of an unsaturated aliphatic hydrocarbon group, the aliphatic hydrocarbon group generally contains preferably 1 to 6, more preferably 1 to 3, further preferably 1 to 2 unsaturated bonds. The unsaturated bond may be a carbon-carbon double bond or a carbon-carbon triple bond, and it is preferably a carbon-carbon double bond. The aforementioned aliphatic hydrocarbon group is preferably an alkyl group or an alkenyl group.

Examples of the aliphatic hydrocarbon group having 12 to 22 carbon atoms include dodecyl group, tridecyl group, tetradecyl group, pentadecyl group, hexadecyl group, heptadecyl group, octadecyl group, nonadecyl group, icosyl group, henicosyl group, docosyl group, dodecenyl group, tridecenyl group, tetradecenyl group, pentadecenyl group, hexadecenyl group, heptadecenyl group, octadecenyl group, nonadecenyl group, icosenyl group, heneicosenyl group, docosenyl group, decadienyl group, tridecadienyl group, tetradecadienyl group, pentadecadienyl group, hexadecadienyl group, heptadecadienyl group, octadecadienyl group, nonadecadienyl group, icosadienoyl group, henicosadienyl group, docosadienyl group, octadecatrienyl group, icosatrienoyl group, icosatetraenoyl group, icosapentaenyl group, docosahexaenoyl group, isostearyl group, 1-hexylheptyl group, 1-hexylnonyl group, 1-octylnonyl group, 1-octylundecyl group, 1-decylundecyl group, and the like. The aliphatic hydrocarbon group having 12 to 22 carbon atoms is preferably a tridecyl group, a pentadecyl group, a heptadecyl group, a nonadecyl group, a heptadecenyl group, a heptadecadienyl group, or a 1-hexylnonyl group, particularly preferably a tridecyl group, a heptadecyl group, a heptadecenyl group, or a heptadecadienyl group.

In one embodiment of the present invention, the aliphatic hydrocarbon group having 12 to 22 carbon atoms for $R^{4a}$ or $R^{4b}$ is derived from fatty acid. In this case, the carbonyl (—CO—) derived from fatty acid is contained in $L^{3a}$, $L^{3b}$, $L^{2a}$, $L^{2b}$, $L^{4a}$, or $L^{4b}$. When oleic acid is used as the fatty acid to form $R^{4a}$ and $R^{4b}$, $R^{4a}$ and $R^{4b}$ are both 8-heptadecenyl groups.

Example of the liposoluble vitamin having a hydroxy group include retinol, ergosterol, 7-dehydrocholesterol, calciferol, cholecalciferol, dihydroergocalciferol, dihydrotachysterol, tocopherol, tocotrienol, and the like. The liposoluble vitamin having a hydroxy group is preferably a tocopherol.

Example of the sterol derivative having a hydroxy group include cholesterol, cholestanol, stigmasterol, β-sitosterol, lanosterol, ergosterol, and the like. The sterol derivative having a hydroxy group is preferably a cholesterol or a cholestanol.

$R^5$ is preferably a residue of a liposoluble vitamin having a hydroxy group. The p is preferably 2.

Preferably, $R^{4a}$ and $R^{4b}$ are each independently an aliphatic hydrocarbon group having 12 to 22 carbon atoms or R—CO—$(CH_2)_p$—, $R^5$ is a liposoluble vitamin having a hydroxy group, and p is 2 or 3; more preferably, $R^{4a}$ and $R^{4b}$ are the same and each is an aliphatic hydrocarbon group having 12 to 22 carbon atoms or R—CO—$(CH_2)_p$—, $R^5$ is a residue of a liposoluble vitamin having a hydroxy group, and p is 2 or 3; further preferably, $R^{4a}$ and $R^{4b}$ are the same and each is an aliphatic hydrocarbon group having 12 to 22 carbon atoms or R—CO—$(CH_2)_p$—, $R^5$ is a residue of a liposoluble vitamin having a hydroxy group (e.g., tocopherol), and p is 2; and particularly preferably, $R^{4a}$ and $R^{4b}$ are the same and each is an aliphatic hydrocarbon group having 12 to 22 carbon atoms.

In one embodiment of the present invention, preferably, $L^{1a}$ is the same as $L^{1b}$, $R^{1a}$ is the same as $R^{1b}$, $X^a$ is the same as $X^b$, $L^{4a}$ is the same as $L^{4b}$, $R^{2a}$ is the same as $R^{2b}$, $L^{2a}$ is the same as $L^{2b}$, $R^{3a}$ is the same as $R^{3b}$, $L^{3a}$ is the same as $L^{3b}$, and $R^{4a}$ is the same as $R^{4b}$.

Preferable examples of the cationic lipid (1) in the present invention include the following cationic lipids.

<Cationic Lipid (1-1)>

Cationic lipid (1) wherein $L^{1a}$ and $L^{1b}$ are both *—NH—CO— (in the aforementioned formula,  indicates a bonding position with $R^{1a}$ or $R^{1b}$, and * indicates a bonding position with a carbon atom on the opposite side from $R^{1a}$ or $R^{1b}$);

$R^{1a}$ and $R^{1b}$ are each independently an alkylene group having not more than 8 carbon atoms;

ka and kb are each independently 0 or 1;

$X^a$ and $X^b$ are each independently a dialkylamino group (the aforementioned two alkyl groups each independently has 1 to 3 carbon atoms), or a 5- or 6-membered cyclic amino group;

$L^{4a}$ and $L^{4b}$ are both *—O—CO—** (in the aforementioned formula, * indicates a bonding position with $R^{2a}$ or $R^{2b}$, and ** indicates a bonding position with $R^{2a}$ or $R^{2b}$).

$R^{2a}$ and $R^{2b}$ are each independently an alkylene group having not more than 8 carbon atoms;

$L^{2a}$ and $L^{2b}$ are both *—CO—O—** (in the aforementioned formula, * indicates a bonding position with $R^{3a}$ or $R^{3b}$, and ** indicates a bonding position with $R^{2a}$ or $R^{2b}$)

ma and mb are both 1;

$R^{3a}$ and $R^{3b}$ are each independently a group represented by the formula (2):

(2)

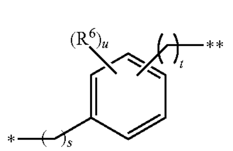

wherein

* indicates a bonding position with $L^{3a}$ or $L^{3b}$,

** indicates a bonding position with $L^{2a}$ or $L^{2b}$, s is an integer of 0 to 3, t is an integer of 0 to 3, u is an integer of 0 to 4, and $R^6$ in the number of u are each independently an acyl group having 2 to 4 carbon atoms, an alkoxycarbonyl group having 2 to 4 carbon atoms, a carbamoyl group having 2 to 4 carbon atoms, an acyloxy group having 2 to 4 carbon atoms, an acylamino group having 2 to 4 carbon atoms, an alkoxycarbonylamino group having 2 to 4 carbon atoms, a fluorine atom, a chlorine atom, a bromine atom, an iodine atom, an alkylsulfanyl group having 1 to 4 carbon atoms, an alkylsulfonyl group having 1 to 4 carbon atoms, an arylsulfonyl group having 6 to 10 carbon atoms, a nitro group, a trifluoromethyl group, a cyano group, an alkyl group having 1 to 4 carbon atoms, a ureido group having 1 to 4 carbon atoms, an alkoxy group having 1 to 4 carbon atoms, an aryl group having 6 to 10 carbon atoms, or an aryloxy group having 6 to 10 carbon atoms;

$L^{3a}$ and $L^{3b}$ are both *—CO—O—** (in the aforementioned formula, * indicates a bonding position with $R^{4a}$ or $R^b$, and ** indicates a bonding position with $R^{3a}$ or $R^b$);

na and nb are both 1; and $R^{4a}$ and $R^{4b}$ are each independently an aliphatic hydrocarbon group having 12 to 22 carbon atoms or $R^5$—CO—$(CH_2)_p$—, $R^5$ is a residue of a liposoluble vitamin having a hydroxy group (e.g., tocopherol), and p is 2 or 3.

<Cationic Lipid (1-2)>

Cationic Lipid (1) Wherein $L^{1a}$ and $L^{1b}$ are both *—NH—CO— (in the aforementioned formula,  indicates a bonding position with $R^{1a}$ or $R^b$, and * indicates a bonding position with a carbon atom on the opposite side from $R^{1a}$ or $R^{1b}$);

$R^{1a}$ and $R^{1b}$ are each independently a methylene group, an ethylene group, a trimethylene group, a tetramethylene group, an isopropylene group ($-CH(CH_3)CH_2-$, $-CH_2CH(CH_3)-$), an isobutylene group ($-C(CH_3)_2CH_2-$, $-CH_2C(CH_3)_2-$), a pentamethylene group, or a hexamethylene group;

ka and kb are each independently 0 or 1;

$X^a$ and $X^b$ are each independently a dimethylamino group, an N-methyl-N-ethylamino group, an N-methyl-N-propylamino group, a diethylamino group, a dipropylamino group, a di(isopropyl)amino group, or a 1-piperidyl group;

$L^{4a}$ and $L^{4b}$ are both *—O—CO—** (in the aforementioned formula, * indicates a bonding position with $R^{2a}$ or $R^{2b}$, and ** indicates a bonding position with $R^{2a}$ or $R^{2b}$);

$R^{2a}$ and $R^{2b}$ are each independently a methylene group, an ethylene group, a trimethylene group, a tetramethylene group, an isobutylene group ($-C(CH_3)_2CH_2-$, $-CH_2C(CH_3)_2-$), a pentamethylene group, or a hexamethylene group;

$L^{2a}$ and $L^{2b}$ are both *—CO—O—** (in the aforementioned formula, * indicates a bonding position with $R^{3a}$ or $R^{3b}$, and ** indicates a bonding position with $R^{2a}$ or $R^{2b}$)

ma and mb are both 1;

$R^{3a}$ and $R^{3b}$ are each independently a group represented by the formula (2):

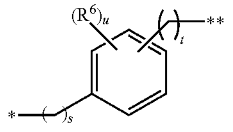
(2)

wherein

* indicates a bonding position with $L^{3a}$ or $L^{3b}$,

** indicates a bonding position with $L^{2a}$ or $L^{2b}$ s is 0 or 1, t is an integer of 0 to 2, u is an integer of 0 to 2, and $R^6$ in the number of u are each independently an acetyl group, a methoxycarbonyl group, a methylcarbamoyl group, an acetoxy group, a acetamido group, a methoxycarbonylamino group, a fluorine atom, a chlorine atom, a bromine atom, an iodine atom, a methylsulfanyl group, a phenylsulfonyl group, a nitro group, a trifluoromethyl group, a cyano group, a methyl group, an ethyl group, a propyl group, an isopropyl group, a tert-butyl group, a ureido group, a methoxy group, an ethoxy group, a propoxy group, an isopropoxy group, a tert-butoxy group, a phenyl group, or a phenoxy group;

$L^{3a}$ and $L^{3b}$ are both *—CO—O—** (in the aforementioned formula, * indicates a bonding position with $R^{4a}$ or $R^{4b}$, and ** indicates a bonding position with $R^{3a}$ or $R^{3b}$);

na and nb are both 1;

$R^{4a}$ and $R^{4b}$ are the same and each is an aliphatic hydrocarbon group having 12 to 22 carbon atoms or $R^5-CO-(CH_2)_p-$, $R^5$ is a residue of a liposoluble vitamin having a hydroxy group (e.g., tocopherol), and p is 2 or 3.

<Cationic Lipid (1-2a)>

Cationic Lipid (1) Wherein $L^{1a}$ and $L^{1b}$ are both *—NH—CO— (in the aforementioned formula,  indicates a bonding position with $R^{1a}$ or $R^{1b}$, and * indicates a bonding position with a carbon atom on the opposite side from $R^{1a}$ or $R^{1b}$);

$R^{1a}$ and $R^{1b}$ are each independently a methylene group, an ethylene group, a trimethylene group, a tetramethylene group, an isopropylene group ($-CH(CH_3)CH_2-$, $-CH_2CH(CH_3)-$), an isobutylene group ($-C(CH_3)_2CH_2-$, $-CH_2C(CH_3)_2-$), a pentamethylene group, or a hexamethylene group;

ka and kb are each independently 0 or 1;

$X^a$ and $X^b$ are each independently a dimethylamino group, an N-methyl-N-ethylamino group, an N-methyl-N-propylamino group, a diethylamino group, or a 1-piperidyl group;

$L^{4a}$ and $L^{4b}$ are both *—O—CO—** (in the aforementioned formula, * indicates a bonding position with $R^{2a}$ or $R^b$, and ** indicates a bonding position with Ra or $R^2$);

$R^{2a}$ and $R^{2b}$ are each independently a methylene group, an ethylene group, a trimethylene group, a tetramethylene group, an isobutylene group ($-C(CH_3)_2CH_2-$, $-CH_2C(CH_3)_2-$), a pentamethylene group, or a hexamethylene group;

$L^{2a}$ and $L^{2b}$ are both *—CO—O—** (in the aforementioned formula, * indicates a bonding position with $R^{3a}$ or $R^{3b}$, and ** indicates a bonding position with $R^{2a}$ or $R^{2b}$)

ma and mb are both 1;

$R^{3a}$ and $R^{3b}$ are each independently a group represented by the formula (2):

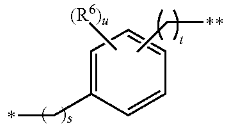
(2)

wherein

* indicates a bonding position with $L^{3a}$ or $L^{3b}$,

** indicates a bonding position with $L^{2a}$ or $L^{2b}$, s is 0 or 1, t is an integer of 0 to 2, u is an integer of 0 to 2, and $R^6$ in the number of u are each independently an acetyl group, a methoxycarbonyl group, a methylcarbamoyl group, an acetoxy group, an acetamido group, a methoxycarbonylamino group, a fluorine atom, a chlorine atom, a bromine atom, an iodine atom, a methylsulfanyl group, a phenylsulfonyl group, an nitro group, a trifluoromethyl group, a cyano group, a methyl group, an ethyl group, a propyl group, an isopropyl group, a tert-butyl group, a ureido group, a methoxy group, an ethoxy group, a propoxy group, an isopropoxy group, a tert-butoxy group, a phenyl group or a phenoxy group;

$L^{3a}$ and $L^{3b}$ are both *—CO—O—** (in the aforementioned formula, * indicates a bonding position with $R^{4a}$ or $R^{4b}$, and ** indicates a bonding position with $R^{3a}$ or $R^{3b}$);

na and nb are both 1;

$R^{4a}$ and $R^{4b}$ are the same and each is an aliphatic hydrocarbon group having 12 to 22 carbon atoms or $R^5$—CO—$(CH_2)_p$—, $R^5$ is a residue of a liposoluble vitamin having a hydroxy group (e.g., tocopherol), and p is 2 or 3.

<Cationic Lipid (1-3)>

Cationic Lipid (1) Wherein $L^{1a}$ and $L^{1b}$ are both *—NH—CO— (in the aforementioned formula,  indicates a bonding position with $R^{1a}$ or $R^{1b}$, and indicates a bonding position with a carbon atom on the opposite side from $R^{1a}$ or $R^{1b}$);

$R^{1a}$ and $R^{1b}$ are each independently a methylene group, an ethylene group, a trimethylene group, an isopropylene group (—$CH(CH_3)CH_2$—, —$CH_2CH(CH_3)$—), a tetramethylene group, or an isobutylene group (—$C(CH_3)_2CH_2$—, —$CH_2C(CH_3)_2$—);

ka and kb are each independently 0 or 1;

$X^a$ and $X^b$ are the same and each is a dimethylamino group, an N-methyl-N-ethylamino group, an N-methyl-N-propylamino group, a diethylamino group, a dipropylamino group, a di(isopropyl)amino group, or a 1-piperidyl group;

$L^{4a}$ and $L^4$ are both *—O—CO—** (in the aforementioned formula, * indicates a bonding position with $R^{2a}$ or $R^{2b}$, and ** indicates a bonding position with $R^{2a}$ or $R^{2b}$);

$R^{2a}$ and $R^{2b}$ are each independently an ethylene group, a trimethylene group, a tetramethylene group, or an isobutylene group (—$C(CH_3)_2CH_2$—, —$CH_2C(CH_3)_2$—);

$L^{2a}$ and $L^{2b}$ are both *—CO—O—** (in the aforementioned formula, * indicates a bonding position with $R^{3a}$ or $R^{3b}$, and ** indicates a bonding position with $R^{2a}$ or $R^{2b}$).

ma and mb are both 1;

$R^{3a}$ and $R^{3b}$ are each independently a group represented by the formula (2):

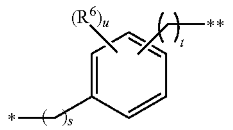

(2)

wherein

* indicates a bonding position with $L^{3a}$ or $L^{3b}$,

** indicates a bonding position with $L^{2a}$ or $L^2$, s is 0, t is 1, and u is 0;

$L^{3a}$ and $L^{3b}$ are both *—CO—O—** (in the aforementioned formula, * indicates a bonding position with $R^{4a}$ or $R^{4b}$, and ** indicates a bonding position with $R^{3a}$ or $R^{3b}$);

na and nb are both 1; and $R^{4a}$ and $R^{4b}$ are the same and each is an aliphatic hydrocarbon group having 12 to 22 carbon atoms or $R^5$—CO—$(CH_2)_p$—, $R^5$ is a residue of a liposoluble vitamin having a hydroxy group (e.g., tocopherol), and p is 2.

<Cationic Lipid (1-3a)>

Cationic Lipid (1) Wherein $L^{1a}$ and $L^{1b}$ are both *—NH—CO— (in the aforementioned formula,  indicates a bonding position with $R^{1a}$ or $R^{1b}$, and * indicates a bonding position with a carbon atom on the opposite side from $R^{1a}$ or $R^{1b}$);

$R^{1a}$ and $R^{1b}$ are each independently a methylene group, an ethylene group, a trimethylene group, an isopropylene group (—$CH(CH_3)CH_2$—, —$CH_2CH(CH_3)$—), a tetramethylene group, or an isobutylene group (—$C(CH_3)_2CH_2$—, —$CH_2C(CH_3)_2$—);

ka and kb are each independently 0 or 1;

$X^a$ and $X^b$ are the same and each is a dimethylamino group, an N-methyl-N-ethylamino group, an N-methyl-N-propylamino group, a diethylamino group, or a 1-piperidyl group;

$L^a$ and $L^b$ are both *—O—CO—** (in the aforementioned formula, * indicates a bonding position with $R^{2a}$ or $R^{2b}$, and ** indicates a bonding position with $R^{2a}$ or $R^{2b}$);

$R^{2a}$ and $R^{2b}$ are each independently an ethylene group, a trimethylene group, a tetramethylene group, or an isobutylene group (—$C(CH_3)_2CH_2$—, —$CH_2C(CH_3)_2$—);

$L^{2a}$ and $L^{2b}$ are both *—CO—O—** (in the aforementioned formula, * indicates a bonding position with $R^{3a}$ or $R^{3b}$, and ** indicates a bonding position with $R^{2a}$ or $R^{2b}$);

ma and mb are both 1;

$R^{3a}$ and $R^{3b}$ are each independently a group represented by the formula (2):

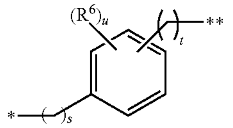

(2)

wherein

* indicates a bonding position with $L^{3a}$ or $L^{3b}$,

** indicates a bonding position with $L^{2a}$ or $L^{2b}$, s is 0, t is 1, and u is 0;

$L^{3a}$ and $L^{3b}$ are both *—CO—O—** (in the aforementioned formula, * indicates a bonding position with $R^{4a}$ or $R^{4b}$, and ** indicates a bonding position with $R^{3a}$ or $R^{3b}$);

na and nb are both 1; and $R^{4a}$ and $R^{4b}$ are the same and each is an aliphatic hydrocarbon group having 12 to 22 carbon atoms or $R^5$—CO—$(CH_2)_p$—, $R^5$ is a residue of a liposoluble vitamin having a hydroxy group (e.g., tocopherol), and p is 2.

<Cationic Lipid (1-3b)>

Cationic Lipid (1) Wherein $L^{1a}$ and $L^{1b}$ are both *—NH—CO— (in the aforementioned formula,  indicates a bonding position with $R^{1a}$ or $R^{1b}$, and * indicates a bonding position with a carbon atom on the opposite side from $R^{1a}$ or $R^{1b}$);

$R^{1a}$ and $R^{1b}$ are both methylene groups;

ka and kb are each independently 0 or 1;

$X^a$ and $X^b$ are the same and each is a dimethylamino group, an N-methyl-N-ethylamino group, an N-methyl-N-propylamino group, a diethylamino group, or a 1-piperidyl group;

$R^{2a}$ and $R^{2b}$ are both ethylene groups;

$L^{2a}$ and $L^{2b}$ are both *—CO—O—** (in the aforementioned formula, * indicates a bonding position with $R^{3a}$ or $R^{3b}$, and ** indicates a bonding position with $R^{2a}$ or $R^{2b}$);

ma and mb are both 1;

$R^{3a}$ and $R^{3b}$ are the same and each is a group represented by the formula (2):

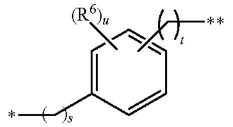

(2)

wherein

* indicates a bonding position with $L^{3a}$ or $L^{3b}$,

** indicates a bonding position with $L^{2a}$ or $L^{2b}$, s is 0, t is 1, and u is 0;

$L^{3a}$ and $L^{3b}$ are both *—CO—O—** (in the aforementioned formula, * indicates a bonding position with $R^{4a}$ or $R^{4b}$, and ** indicates a bonding position with $R^{3a}$ or $R^{3b}$);

na and nb are both 1;

$R^{4a}$ and $R^{4b}$ are the same and each is an aliphatic hydrocarbon group having 12 to 22 carbon atoms.

<Cationic Lipid (1-4)>

Cationic Lipid (1) Wherein $L^{1a}$ and $L^{1b}$ are both *—NH—CO— (in the aforementioned formula,  indicates a bonding position with $R^{1a}$ or $R^{1b}$, and * indicates a bonding position with a carbon atom on the opposite side from $R^{1a}$ or $R^{1b}$);

$R^{1a}$ and $R^{1b}$ are both methylene groups;

ka and kb are each independently 0 or 1;

$X^a$ and $X^b$ are both dimethylamino groups;

$R^{2a}$ and $R^{2b}$ are both ethylene groups;

$L^{2a}$ and $L^{2b}$ are both *—CO—O—** (in the aforementioned formula, * indicates a bonding position with $R^{3a}$ or $R^{3b}$, and ** indicates a bonding position with $R^{2a}$ or $R^{2b}$);

ma and mb are both 1;

$R^{3a}$ and $R^{3b}$ are the same and each is a group represented by the formula (2):

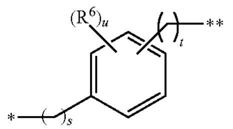

(2)

wherein

* indicates a bonding position with $L^{3a}$ or $L^{2b}$,

** indicates a bonding position with $L^{2a}$ or $L^{2b}$, s is 0, t is 1, and u is 0;

$L^{3a}$ and $L^{3b}$ are both *—CO—O—** (in the aforementioned formula, * indicates a bonding position with $R^{4a}$ or $R^{4b}$, and ** indicates a bonding position with $R^{3a}$ or $R^{3b}$);

na and nb are both 1; and $R^{4a}$ and $R^{4b}$ are the same and each is an aliphatic hydrocarbon group having 12 to 22 carbon atoms.

The cationic lipid of the present invention (1) sometimes containing a stereoisomer and a geometric isomer. Unless particularly indicated, the cationic lipid (1) of the present invention includes isomers thereof. In addition, the cationic lipid (1) of the present invention may be a mixture of plural isomers. In a mixture of plural isomers, the ratio of each isomer is not particularly limited.

Specific examples of the cationic lipid (1) of the present invention include the following O-Ph-cys-C2-DMA, O-Ph-cys-C2-EMA, O-Ph-cys-C2-MPA, O-Ph-cys-C2-DEA, O-Ph-cys-C2-DPA, O-Ph-cys-C2-DIA, O-Ph-cys-C2-Pip, E-Ph-cys-C2-DMA, O-Ph-cys-C4-DMA, and O-Ph-cys-DMA. The cationic lipid (1) of the present invention is preferably at least one selected from the group consisting of these, more preferably at least one selected from the group consisting of O-Ph-cys-C2-DMA, O-Ph-cys-C2-EMA, O-Ph-cys-C2-MPA, O-Ph-cys-C2-DEA, and O-Ph-cys-C2-Pip, most preferably O-Ph-cys-C2-DMA.

TABLE 1

| name of cationic lipid | structure |
|---|---|
| O-Ph-cys-C2-DMA | 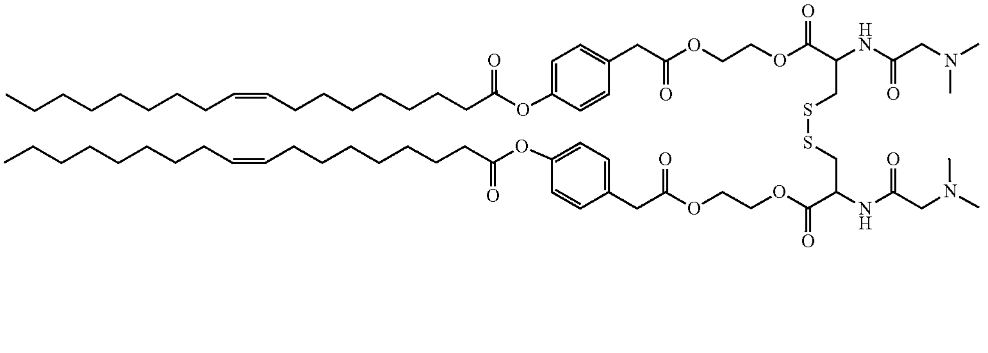 [SMILES: CCCCCCCC/C=C\CCCCCCCC(=O)Oc1ccc(CC(=O)OCCOC(=O)C(CSSCC(NC(=O)CN(C)C)C(=O)OCCOC(=O)Cc2ccc(OC(=O)CCCCCCC/C=C\CCCCCCCC)cc2)NC(=O)CN(C)C)cc1] |

TABLE 1-continued
| name of cationic lipid | structure |
|---|---|
| O-Ph-cys-C2-EMA | 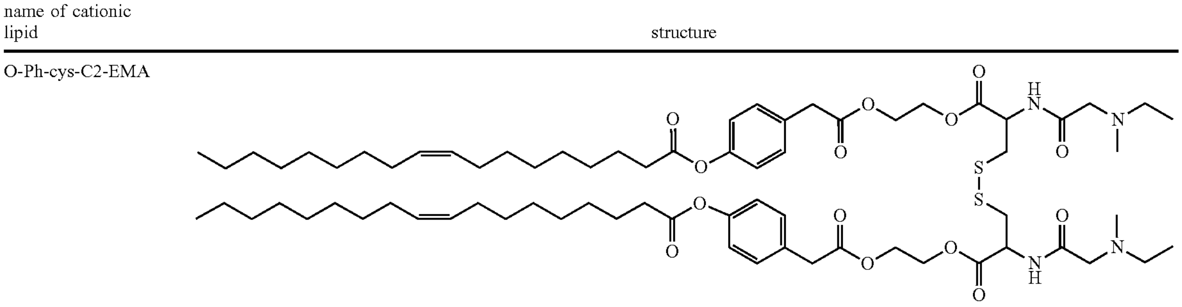 |
| O-Ph-cys-C2-MPA | 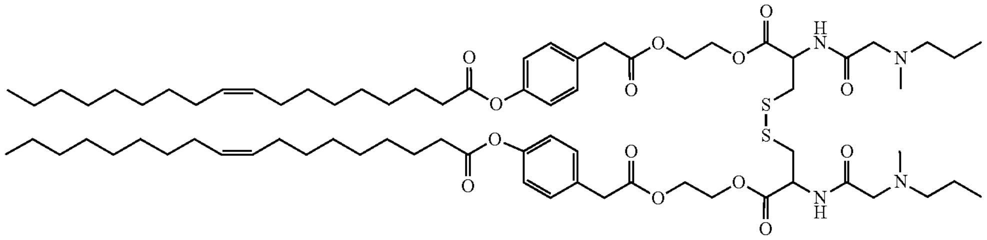 [SMILES: CCCCCCCC/C=C\CCCCCCCC(=O)Oc1ccc(CC(=O)OCCOC(=O)C(CSSCC(NC(=O)CN(C)CCC)C(=O)OCCOC(=O)Cc2ccc(OC(=O)CCCCCCC/C=C\CCCCCCCC)cc2)NC(=O)CN(C)CCC)cc1] |
| O-Ph-cys-C2-DEA | 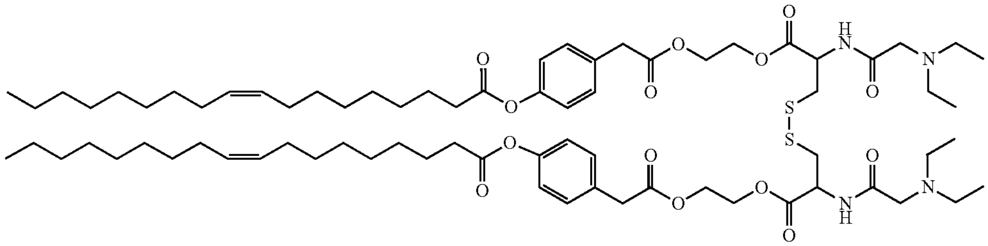 [SMILES: CCCCCCCC/C=C\CCCCCCCC(=O)Oc1ccc(CC(=O)OCCOC(=O)C(CSSCC(NC(=O)CN(CC)CC)C(=O)OCCOC(=O)Cc2ccc(OC(=O)CCCCCCC/C=C\CCCCCCCC)cc2)NC(=O)CN(CC)CC)cc1] |
| O-Ph-cys-C2-DPA | 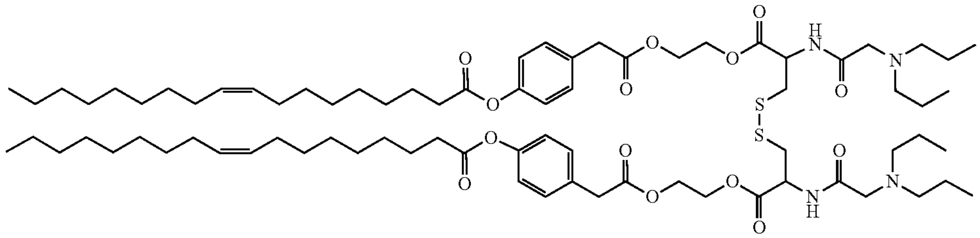 [SMILES: CCCCCCCC/C=C\CCCCCCCC(=O)Oc1ccc(CC(=O)OCCOC(=O)C(CSSCC(NC(=O)CN(CCC)CCC)C(=O)OCCOC(=O)Cc2ccc(OC(=O)CCCCCCC/C=C\CCCCCCCC)cc2)NC(=O)CN(CCC)CCC)cc1] |
TABLE 2
| name of cationic lipid | structure |
|---|---|
| O-Ph-cys-C2-DIA | 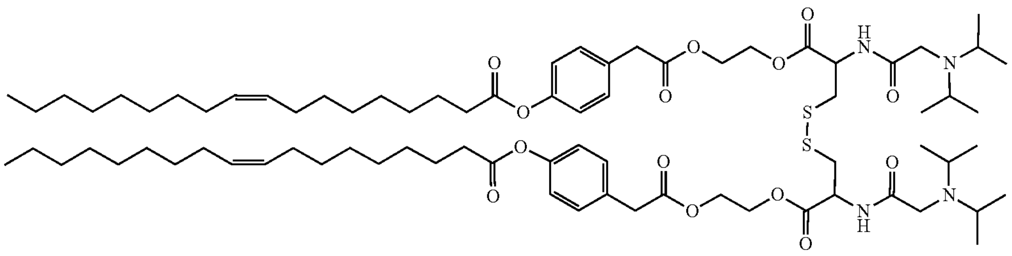 [SMILES: CCCCCCCC/C=C\CCCCCCCC(=O)Oc1ccc(CC(=O)OCCOC(=O)C(CSSCC(NC(=O)CN(C(C)C)C(C)C)C(=O)OCCOC(=O)Cc2ccc(OC(=O)CCCCCCC/C=C\CCCCCCCC)cc2)NC(=O)CN(C(C)C)C(C)C)cc1] |

TABLE 2-continued

| name of cationic lipid | structure |
| --- | --- |
| O-Ph-cys-C2-Pip | 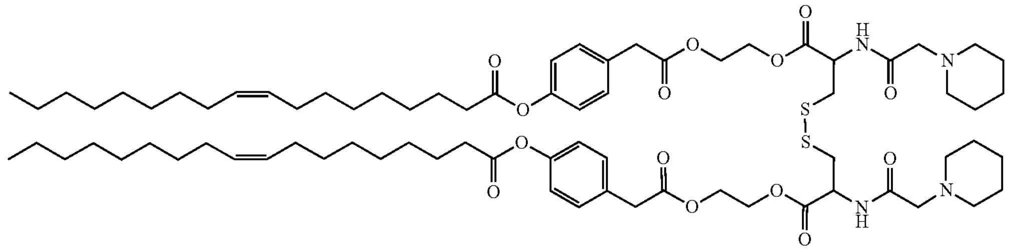 [SMILES: CCCCCCCC/C=C\CCCCCCCC(=O)Oc1ccc(CC(=O)OCCOC(=O)C(CSSCC(NC(=O)CN2CCCCC2)C(=O)OCCOC(=O)Cc2ccc(OC(=O)CCCCCCC/C=C\CCCCCCCC)cc2)NC(=O)CN2CCCCC2)cc1] |
| E-Ph-cys-C2-DMA | 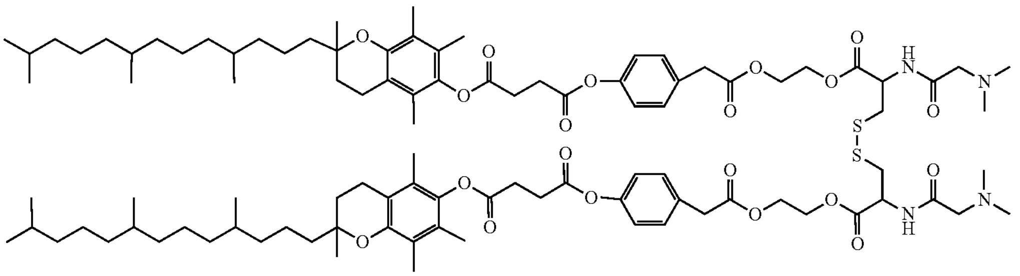 [SMILES: Cc1c(C)c2c(c(C)c1OC(=O)CCC(=O)Oc1ccc(CC(=O)OCCOC(=O)C(CSSCC(NC(=O)CN(C)C)C(=O)OCCOC(=O)Cc3ccc(OC(=O)CCC(=O)Oc4c(C)c(C)c5c(c4C)CCC(C)(CCCC(C)CCCC(C)CCCC(C)C)O5)cc3)NC(=O)CN(C)C)cc1)CCC(C)(CCCC(C)CCCC(C)CCCC(C)C)O2] |
| O-Ph-cys-C4-DMA | 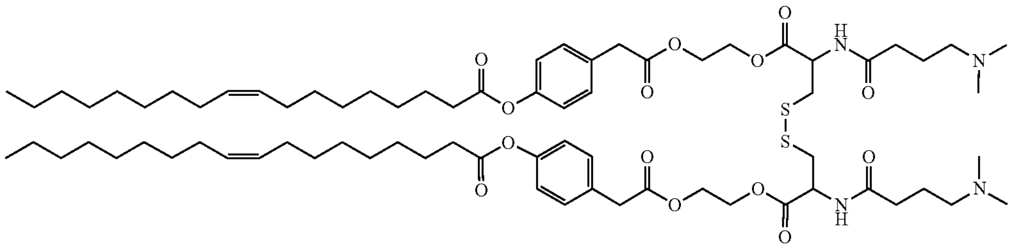 [SMILES: CCCCCCCC/C=C\CCCCCCCC(=O)Oc1ccc(CC(=O)OCCOC(=O)C(CSSCC(NC(=O)CCCN(C)C)C(=O)OCCOC(=O)Cc2ccc(OC(=O)CCCCCCC/C=C\CCCCCCCC)cc2)NC(=O)CCCN(C)C)cc1] |
| O-Ph-cys-DMA | 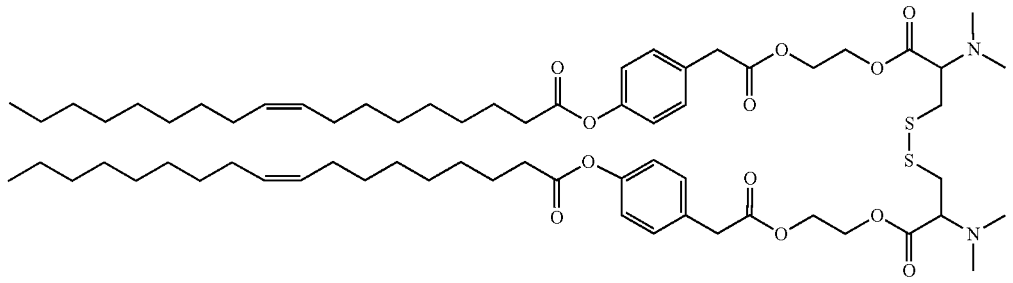 [SMILES: CCCCCCCC/C=C\CCCCCCCC(=O)Oc1ccc(CC(=O)OCCOC(=O)C(CSSCC(C(=O)OCCOC(=O)Cc2ccc(OC(=O)CCCCCCC/C=C\CCCCCCCC)cc2)N(C)C)N(C)C)cc1] |

The production method of the cationic lipid (1) of the present invention is described now.

The cationic lipid (1) in the present invention has an —S—S— (disulfide) bond. Therefore, the production method of the cationic lipid (1) of the present invention includes (A) a method including producing a thiol represented by $\{R^{4a}\text{-}(L^{3a}\text{-}R^{3a})_{na}\text{-}(L^{2a}\text{-}R^{2a})_{ma}\text{-}L^{4a}\text{-}\}CH(CH_2SH)\{\text{-}(L^{1a}\text{-}R^{1a})_{ka}\text{—}X^a\}$ and a thiol represented by $\{R^{4b}\text{-}(L^{3b}\text{-}R^{3b})_{nb}\text{-}(L^{2b}\text{-}R^{2b})_{mb}\text{-}L^{4b}\text{-}\}CH(CH_2SH)\{\text{-}(L^{1b}\text{-}R^{1b})_{kb}\text{—}X^b\}$, and subjecting them to oxidation and coupling, (B) a method including sequentially bonding necessary parts to a starting compound containing an —S—S— bond to finally obtain the cationic lipid (1) of the present invention, and the like. The production method of the cationic lipid (1) of the present invention is preferably the method of the aforementioned (B).

The method of the aforementioned (B) is described below; however, the production method of the cationic lipid (1) of the present invention is not limited thereto.

Examples of the starting compound containing an —S—S— bond include cystine, L-cystine and a salt thereof, N,N,N',N'-tetramethyl-L-cystine and a salt thereof, compound in which an amino group at the both terminals of cystine is protected by a 9-fluorenylmethyloxycarbonyl group, a tert-butoxycarbonyl group, a benzyloxycarbonyl group, an acetyl group, or the like and a salt thereof, compound in which a carboxy group at the both terminals of cystine is protected by a methyl group, an allyl group, or the like, and the like.

For example, when cationic lipid (1) wherein $L^{1a}$ and $L^{1b}$ are both $L^1$, $R^{1a}$ and $R^{1b}$ are both $R^1$, ka and kb are both 1, $X^a$ and $X^b$ are both X, $L^{4a}$ and $L^{4b}$ are both $L^4$, $R^{2a}$ and $R^{2b}$ are both $R^2$, $L^{2a}$ and $L^{2b}$ are both $L^2$, ma and mb are both 1, $R^{3a}$ and $R^{3b}$ are both $R^3$, $L^{3a}$ and $L^{3b}$ are both $L^3$, na and nb are both 1, and $R^{4a}$ and $R^{4b}$ are both $R^4$ is produced, a cationic lipid represented by the following formula (1') can be obtained by the synthesis pathway shown below.

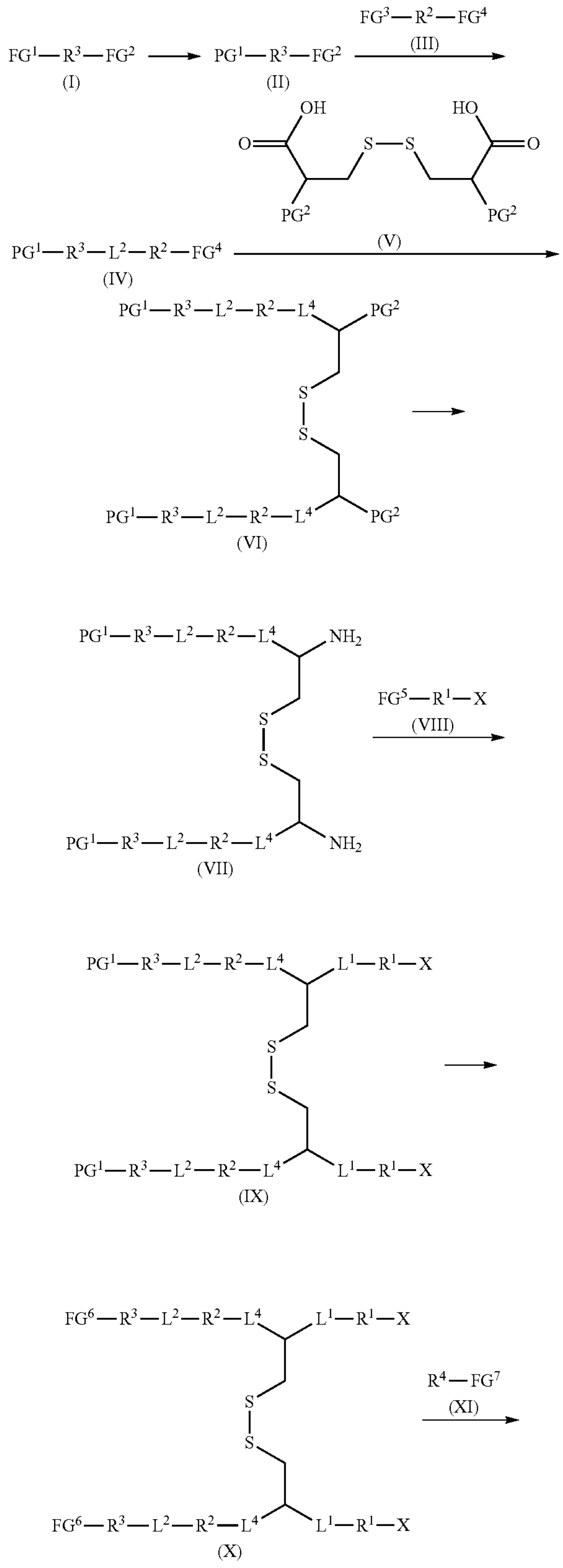

(I)
(II)
(IV)
(VI)
(VII)
(IX)
(X)

-continued

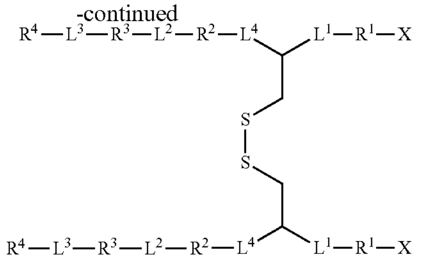

(1')

One ($FG^1$) of reactive functional groups ($FG^1$ and $FG^2$) in compound (I) having $R^3$ and the reactive functional groups at the terminal is reacted with a reagent for introducing a protecting group to synthesize compound (II) having a protected functional group ($PG^1$). The reactive functional group ($FG^2$) in compound (II) is reacted with one ($FG^3$) of reactive functional groups ($FG^3$ and $FG^4$) in compound (III) having $R^2$ and the reactive functional groups at the terminal to synthesize compound (IV). The reactive functional group ($FG^4$) in compound (IV) is reacted with a carboxy group at the terminal of cystine (V) having a protected amino group ($PG^2$) to synthesize compound (VI). The protecting group is removed from the protected amino group ($PG^2$) of compound (VI) to synthesize compound (VII) having an amino group at the terminal. The amino group at the terminal of compound (VII) is reacted with a reactive functional group ($FG^5$) in compound (VIII) having $R^1$, and X and the reactive functional group ($FG^5$) at the terminal to synthesize compound (IX). The protecting group is removed from the protected functional group ($PG^1$) of compound (IX) to synthesize compound (X) having a reactive functional group ($FG^6$) at the terminal. Finally, the reactive functional group ($FG^6$) of compound (X) is reacted with a reactive functional group ($FG^7$) in compound (XI) having $R^4$ and the reactive functional group ($FG^7$), whereby cationic lipid (1') having a cystine skeleton, $L^1$, $R^1$, X, $L^4$, $R^2$, $L^2$, $R^3$, $L^3$, and $R^4$ can be obtained.

The protection and deprotection of the reactive functional groups in the aforementioned synthetic pathway can be performed using known reagents and methods (e.g., the reagents and methods described in GREENE'S PROTECTIVE GROUPS IN ORGANIC SYNTHESIS, 4th Edition, WILEY-INTERSCIENCEM).

The solvent to be used for the protection reaction of the reactive functional group ($FG^1$) of compound (I) (reaction to form compound (II) from compound (I)) is not particularly limited as long as it does not inhibit the reaction. Examples of the aforementioned solvent include water, ethyl acetate, dichloromethane, chloroform, acetonitrile, tetrahydrofuran, dimethylformamide, dimethyl sulfoxide, toluene, and the like. Among these, dichloromethane, chloroform, and toluene are preferred.

Examples of the protecting groups used for protecting the reactive functional group ($FG^1$) in compound (I) include acetal protecting group, silyl protecting group, ester protecting group, ether protecting group, and the like. Among these, an acetal protecting group is preferred. Examples of the reagent forming a protecting group include 3,4-dihydro-2H-pyran and the like.

In the reaction to form compound (II) from compound (I), a catalyst may be used. The catalyst to be used can be appropriately selected according to the type of the compound to be reacted.

The reaction temperature to form compound (II) from compound (I) is generally 0 to 150° C., preferably 0 to 80° C., more preferably 10 to 50° C. The reaction time is generally 1 to for 48 hr, preferably 1 to for 24 hr.

The compound (II) obtained by a protection reaction of the reactive functional group ($FG^1$) of compound (I) can be appropriately purified by a general purification method such as extraction, recrystallization, adsorption, reprecipitation, column chromatography, ion exchange chromatography, and the like.

The reaction between compound (II) and compound (III) may be performed without using a catalyst, or may be performed in the presence of a catalyst. The catalyst to be used in the reaction between compound (II) and compound (III) can be appropriately selected according to the type of the compound to be reacted. As the aforementioned catalyst, base catalysts such as potassium carbonate, sodium carbonate, potassium hydroxide, triethylamine, 4-dimethylaminopyridine (hereinafter sometimes to be abbreviated as "DMAP"), and the like may be used, and acid catalysts such as p-toluenesulfonic acid, methanesulfonic acid, and the like may be used.

For the reaction between compound (II) and compound (III), condensing agents such as dicyclohexylcarbodiimide (hereinafter sometimes to be abbreviated as "DCC"), diisopropyl carbodiimide (hereinafter sometimes to be abbreviated as "DIC"), 1-ethyl-3-(3-dimethylaminopropyl)carbodiimide hydrochloride (hereinafter sometimes to be abbreviated as "EDC"), and the like may be used. Compound (II) may be converted to an anhydride or the like using a condensing agent, and the obtained anhydride or the like may be reacted with compound (III).

The solvent to be used for the reaction between compound (II) and compound (III) is not particularly limited as long as it does not inhibit the reaction. Examples of the aforementioned solvent include water, ethyl acetate, dichloromethane, chloroform, acetonitrile, tetrahydrofuran, dimethylformamide, dimethyl sulfoxide, toluene, and the like. Among these, tetrahydrofuran is preferred.

The temperature of the reaction between compound (II) and compound (III) is generally 0 to 150° C., preferably 0 to 80° C., more preferably 10 to 50° C. The reaction time thereof is generally 1 to 48 hr, preferably 1 to 24 hr.

Compound (IV) obtained by the reaction between compound (II) and compound (III) can be appropriately purified by a general purification method such as extraction, recrystallization, adsorption, reprecipitation, column chromatography, ion exchange chromatography, and the like.

The reaction between compound (IV) and compound (V) may be performed without using a catalyst, or may be performed in the presence of a catalyst. The catalyst to be used in the reaction between compound (IV) and compound (V) can be appropriately selected according to the type of the compound to be reacted. As the aforementioned catalyst, base catalysts such as potassium carbonate, sodium carbonate, potassium hydroxide, triethylamine, DMAP, and the like may be used, and acid catalysts such as p-toluenesulfonic acid, methanesulfonic acid, and the like may be used.

For the reaction between compound (IV) and compound (V), condensing agents such as DCC, DIC, EDC, and the like may be used. Compound (V) may be converted to an anhydride or the like using a condensing agent, and the obtained anhydride or the like may be reacted with compound (IV).

The solvent to be used for the reaction between compound (IV) and compound (V) is not particularly limited as long as it does not inhibit the reaction. Examples of the aforementioned solvent include water, ethyl acetate, dichloromethane, chloroform, acetonitrile, tetrahydrofuran, dimethylformamide, dimethyl sulfoxide, toluene, and the like. Among these, tetrahydrofuran is preferred.

The temperature of the reaction between compound (IV) and compound (V) is generally 0 to 150° C., preferably 0 to 80° C., more preferably 10 to 50° C. The reaction time is generally 1 to 48 hr, preferably 1 to 24 hr.

Compound (VI) obtained by the reaction between compound (IV) and compound (V) can be appropriately purified by a general purification method such as extraction, recrystallization, adsorption, reprecipitation, column chromatography, ion exchange chromatography, and the like.

The solvent to be used for the reaction to remove the protecting group of amino group of compound (VI) (i.e., reaction to form compound (VII) from compound (VI)) is not particularly limited as long as it does not inhibit the reaction. Examples of the aforementioned solvent include water, ethyl acetate, dichloromethane, chloroform, acetonitrile, tetrahydrofuran, dimethylformamide, dimethyl sulfoxide, toluene, methanol, ethanol, isopropanol, and the like. Among these, tetrahydrofuran is preferred.

The reagent to be used to remove the protecting group of amino group of compound (VI) can be appropriately selected according to the protecting group.

The temperature of the reaction to form compound (VII) from compound (VI) is generally 0 to 150° C., preferably 0 to 80° C., more preferably 10 to 50° C. The reaction time is generally 1 to 48 hr, preferably 1 to for 24 hr.

Compound (VII) obtained by the reaction to remove the protecting group from the amino group of compound (VI) can be appropriately purified by a general purification method such as extraction, recrystallization, adsorption, reprecipitation, column chromatography, ion exchange chromatography, and the like.

The reaction between compound (VII) and compound (VIII) may be performed without using a catalyst, or may be performed in the presence of a catalyst. The catalyst to be used in the reaction between compound (VII) and compound (VIII) can be appropriately selected according to the type of the compound to be reacted. As the aforementioned catalyst, base catalysts such as potassium carbonate, sodium carbonate, potassium hydroxide, triethylamine, DMAP, and the like may be used, and acid catalysts such as p-toluenesulfonic acid, methanesulfonic acid, and the like may be used.

For the reaction between compound (VII) and compound (VIII), condensing agents such as DCC, DIC, EDC, and the like may be used. Compound (VIII) may be converted to an anhydride or the like using a condensing agent, and the obtained anhydride or the like may be reacted with compound (VII).

The solvent to be used for the reaction between compound (VII) and compound (VIII) is not particularly limited as long as it does not inhibit the reaction. Examples of the aforementioned solvent include water, ethyl acetate, dichloromethane, chloroform, acetonitrile, tetrahydrofuran, dimethylformamide, dimethyl sulfoxide, toluene, methanol, ethanol, isopropanol, and the like. Among these, dichloromethane and chloroform are preferred.

The reaction temperature of compound (VII) and compound (VIII) is generally 0 to 150° C., preferably 0 to 80° C., more preferably 10 to 50° C. The reaction time is generally 1 to 48 hr, preferably 1 to 24 hr.

Compound (IX) obtained by the reaction between compound (VII) and compound (VIII) can be appropriately purified by a general purification method such as extraction, recrystallization, adsorption, reprecipitation, column chromatography, ion exchange chromatography, and the like.

The solvent to be used for the reaction to remove the protecting group from the protected functional group ($PG^1$) of compound (IX) (i.e., reaction to form compound (X) from compound (IX)) is not particularly limited as long as it does not inhibit the reaction. Examples of the aforementioned solvent include water, ethyl acetate, dichloromethane, chloroform, acetonitrile, tetrahydrofuran, dimethylformamide, dimethyl sulfoxide, toluene, methanol, ethanol, isopropanol, and the like. Among these, water is preferred.

The reagent to be used for the reaction to remove the protecting group from the protected functional group ($PG^1$) of compound (IX) can be appropriately selected according to the protecting group.

The reaction temperature to form compound (X) from compound (IX) is generally 0 to 150° C., preferably 0 to 80° C., more preferably 10 to 50° C. The reaction time is generally 1 to 48 hr, preferably 1 to 24 hr.

Compound (X) obtained by the reaction to remove the protecting group from the protected functional group ($PG^1$) of compound (IX) can be appropriately purified by a general purification method such as extraction, recrystallization, adsorption, reprecipitation, column chromatography, ion exchange chromatography, and the like.

The reaction between compound (X) and compound (XI) may be performed without using a catalyst, or may be performed in the presence of a catalyst. The catalyst to be used in the reaction between compound (X) and compound (XI) can be appropriately selected according to the type of the compound to be reacted. As the aforementioned catalyst, base catalysts such as potassium carbonate, sodium carbonate, potassium hydroxide, triethylamine, DMAP, and the like may be used, and acid catalysts such as p-toluenesulfonic acid, methanesulfonic acid, and the like may be used.

For the reaction between compound (X) and compound (XI), condensing agents such as DCC, DIC, EDC, and the like may be used. Compound (XI) may be converted to an anhydride or the like using a condensing agent, and the obtained anhydride or the like may be reacted with compound (X).

The solvent to be used for the reaction between compound (X) and compound (XI) is not particularly limited as long as it does not inhibit the reaction. Examples of the aforementioned solvent include water, ethyl acetate, dichloromethane, chloroform, acetonitrile, tetrahydrofuran, dimethylformamide, dimethyl sulfoxide, toluene, and the like. Among these, dichloromethane and chloroform are preferred.

The reaction temperature of compound (X) and compound (XI) is generally 0 to 150° C., preferably 0 to 80° C., more preferably 10 to 50° C. The reaction time is generally 1 to 48 hr, preferably 1 to 24 hr.

Cationic lipid (1') obtained by the reaction between compound (X) and compound (XI) can be appropriately purified by a general purification method such as extraction, recrystallization, adsorption, reprecipitation, column chromatography, ion exchange chromatography, and the like.

Specific production methods are described in Examples 1 to 10 describe later. Those of ordinary skill in the art can produce a desired cationic lipid (1) by appropriately selecting the starting material and performing the reaction according to the methods described in Examples 1 to 10.

The lipid membrane structure of the present invention is now described.

The lipid membrane structure of the present invention contains the cationic lipid (1) of the present invention as a membrane-constituting material. As used herein, the "lipid membrane structure" in the present invention means a structure having a membrane structure in which the hydrophilic groups of amphipathic lipid are arranged in the interface, facing the aqueous phase side. The "amphiphilic lipid" means a lipid having both a hydrophilic group and a hydrophobic group. Examples of the amphiphilic lipid include cationic lipid, phospholipid, and the like.

While the form of the lipid membrane structure of the present invention is not particularly limited, for example, liposome (e.g., monolayer liposome, multilayer liposome, and the like), O/W emulsion, W/O emulsion, spherical micelle, worm-like micelle, lipid nano particles (LNP), disordered layer structure, and the like can be mentioned as a form of the cationic lipid (1) of the present invention dispersed in an aqueous solvent. The lipid membrane structure of the present invention is preferably LNP.

The lipid membrane structure of the present invention may further contain other constituent components in addition to the cationic lipid (1) of the present invention. Examples of other constituent component include lipid (phospholipid (phosphatidylinositol, phosphatidylethanolamine, phosphatidylserine, phosphatidic acid, phosphatidylglycerol, phosphatidylcholine, and the like), glycolipid, peptide lipid, cholesterol, cationic lipid other than the cationic lipid (1) of the present invention, PEG lipid, and the like), surfactant (e.g., 3-[(3-cholamidopropyl)dimethylammonio]propanesulfonate, sodium cholate salt, octylglycoside, N-D-gluco-N-methylalkanamides, and the like), polyethylene glycol, protein, and the like. The content of other constituent components in the lipid membrane structure of the present invention is preferably 5 to 95 mol %, more preferably 10 to 90 mol %, further preferably 30 to 80 mol %, with respect to all constituent components in the lipid membrane structure of the present invention (i.e., total of the cationic lipid (1) of the present invention and other constituent components).

While the content of the cationic lipid (1) of the present invention in the lipid membrane structure of the present invention is not particularly limited, when the lipid membrane structure is used as the below-mentioned nucleic acid-introducing agent, the cationic lipid (1) of the present invention is contained in an amount sufficient for introducing a nucleic acid. For example, the content of the cationic lipid (1) of the present invention in the lipid membrane structure of the present invention is preferably 5 to 100 mol %, more preferably 10 to 90 mol %, further preferably 20 to 70 mol %, with respect to all lipids in the lipid membrane structure of the present invention.

The lipid membrane structure of the present invention can be prepared by dispersing the cationic lipid (1) of the present invention and other constituent components (lipid and the like) in a suitable solvent or dispersion medium, for example, aqueous solvent and alcoholic solvent, and performing an operation to induce organization as necessary.

Examples of the "operation to induce organization" include, but are not limited to, methods known per se such as ethanol dilution method using a micro flow path or vortex, simple hydration method, sonication, heating, vortex, ether injecting method, French press method, cholic acid method, $Ca^{2+}$ fusion method, freeze-thaw method, reversed-phase evaporation method, and the like.

A nucleic acid can be introduced into a cell in vivo and/or in vitro by encapsulating the nucleic acid in the lipid membrane structure containing the cationic lipid of the present invention and contacting the lipid membrane structure with the cell. Therefore, the present invention provides a nucleic acid-introducing agent, containing the above-mentioned cationic lipid (1) or lipid membrane structure of the present invention.

The nucleic acid-introducing agent of the present invention can introduce any nucleic acid into a cell. While any of single-stranded to triple-stranded nucleic acids can be used, single-stranded or double-strand one is preferred.

Examples of the nucleic acid include, but are not limited to, DNA, RNA, chimera nucleic acid of RNA, DNA/RNA hybrid, and the like. Nucleic acids other than DNA, RNA, chimera nucleic acid of RNA, and DNA/RNA hybrid may also be used (hereinafter to be indicated as "other nucleic acid"). Examples of other nucleic acid include nucleotides having N-glycoside of a purine or pyrimidine base, oligomers having a non-nucleotide backbone (e.g., commercially available peptide nucleic acid (PNA) and the like), oligomers containing a special bond (said oligomer containing a nucleotide having a base pairing or a configuration permitting attachment of base, which are found in DNA and RNA), and the like.

Furthermore, the nucleic acid may also be, for example, a nucleic acid added with known modification, a nucleic acid with a label known in the pertinent field, a nucleic acid with a cap, a methylated nucleic acid, a nucleic acid in which one or more natural nucleotides substituted by an analog, a nucleic acid with intramolecularly crosslinked nucleotide, a nucleic acid with a non-charge bond (e.g., methylphosphonate, phosphotriester, phosphoramidate, carbamate, and the like), a nucleic acid with a charged bond or sulfur-containing bond (e.g., phosphorothioate, phosphorodithioate, and the like), for example, a nucleic acid with a side chain group such as protein (nuclease, nuclease inhibitor, toxin, antibody, signal peptide, poly-L-lysine, and the like), sugar (e.g., monosaccharide and the like), and the like, a nucleic acid containing an intercalating compound (e.g., acridine, psoralen, and the like), a nucleic acid with a chelate compound (e.g., metal, radioactive metal, boron, oxidative metal, and the like), a nucleic acid containing an alkylating agent, a nucleic acid with a modified bond (e.g., a anomer-type nucleic acid and the like), or the like.

The type of the DNA that can be used in the present invention is not particularly limited, and can be selected as appropriate according to the purpose of use. Examples of the DNA include plasmid DNA, cDNA, antisense DNA, chromosomal DNA, PAC, BAC, CpG oligo, and the like. Among these, plasmid DNA, cDNA, and antisense DNA are preferred, and plasmid DNA is more preferred. Circular DNA such as plasmid DNA and the like can be digested as appropriate with restriction enzymes and the like, and also used as a linear DNA.

The type of the RNA that can be used in the present invention is not particularly limited, and can be selected as appropriate according to the purpose of use. Examples of the RNA include siRNA, miRNA, shRNA, antisense RNA, messenger RNA (mRNA), single strand RNA genome, double strand RNA genome, RNA replicon, transfer RNA, ribosomal RNA, and the like. Among these, siRNA, miRNA, shRNA, mRNA, antisense RNA, and RNA replicon are preferred.

The nucleic acid used in the present invention is preferably purified by a method generally used by those of ordinary skill in the art.

The nucleic acid-introducing agent of the present invention encapsulating a nucleic acid can be administered in vivo for the purpose of, for example, prevention and/or treatment of diseases. Therefore, the nucleic acid to be used in the present invention is preferably one having a preventive and/or therapeutic activity against a given disease (prophylactic/therapeutic nucleic acid). Examples of such nucleic acid include nucleic acids used for so-called gene therapy, and the like.

The lipid membrane structure of the present invention encapsulating a nucleic acid (i.e., the nucleic acid-introducing agent of the present invention encapsulating the nucleic acid) can be formed by achieving the co-presence of the nucleic acid of interest and the constituent components (lipid and the like) of the lipid membrane structure of the present invention when forming the lipid membrane structure of the present invention.

For example, when the lipid membrane structure of the present invention is formed as a liposome by an ethanol dilution method, an aqueous nucleic acid solution and an ethanol solution of the constituent components (lipid and the like) of the lipid membrane structure are vigorously mixed in a vortex, micro flow path, or the like, and the obtained mixture is diluted with an appropriate buffer, whereby the lipid membrane structure of the present invention encapsulating a nucleic acid (i.e., the nucleic acid-introducing agent of the present invention encapsulating a nucleic acid) can be formed.

In addition, when the lipid membrane structure of the present invention is formed as a liposome by a simple hydration method, the constituent components of the lipid membrane structure are dissolved in an appropriate organic solvent, and the solution is placed in a glass container and dried under reduced pressure to evaporate the solvent, whereby a lipid thin film is obtained. Then, to the obtained lipid thin film is added an aqueous nucleic acid solution and after hydration, the mixture is sonicated by a sonicator, whereby the lipid membrane structure of the present invention encapsulating the nucleic acid (i.e., the nucleic acid-introducing agent of the present invention encapsulating the nucleic acid) can be formed.

One form of the lipid membrane structure of the present invention encapsulating a nucleic acid is LNP encapsulating the nucleic acid by forming an electrostatic complex between the nucleic acid and a cationic lipid. This LNP can be used for a drug delivery system for selectively delivering a nucleic acid and the like into a particular cell, and is useful for, for example, DNA vaccines, gene therapy drugs for tumor, nucleic acid pharmaceutical products that suppress expression of target genes by utilizing RNA interference, and the like, based on introduction of antigen gene into dendritic cells.

The particle size of the lipid membrane structure of the present invention encapsulating a nucleic acid is not particularly limited, and is preferably 10 nm to 500 nm, more preferably 30 nm to 300 nm. The particle size can be measured by using a particle size distribution measuring device such as Zetasizer Nano (Malvern) and the like. The particle size of the lipid membrane structure can be appropriately adjusted by the method for preparing the lipid membrane structure.

The zeta potential of the lipid membrane structure of the present invention encapsulating a nucleic acid is not particularly limited and preferably −15 to +15 mV, more preferably −10 to +10 mV. In conventional gene transfer, particles electrically charged to have a plus surface potential have been mainly used. This is useful as a method for promoting electrostatic interactions with negatively-charged heparin sulfate on the cell surface to enhance uptake into cells. However, the positive surface charge may suppress (a) release of nucleic acid from the carrier in the cell due to the interaction with a nucleic acid to be delivered, or (b) protein synthesis due to the interaction between mRNA and a nucleic acid to be delivered. This problem can be solved by adjusting the zeta potential to fall within the above-mentioned range. The zeta potential can be measured using a zeta potential measuring apparatus such as Zetasizer Nano and the like. The zeta potential of the lipid membrane structure can be adjusted by the composition of the constituent component of the lipid membrane structure containing the cationic lipid (1) of the present invention.

The lipid membrane surface pKa (hereinafter sometimes to be abbreviated as "Liposomal pKa") of the lipid membrane structure of the present invention is not particularly limited, and the pKa is preferably 5.0 to 7.2, further preferably 6.0 to 6.8. Liposomal pKa is used as an index indicating the susceptibility of protonation of a lipid membrane structure which is incorporated by endocytosis in an endosome in a weakly acidic environment inside the endosome. As described in non-Patent Literatures 2 and 3, to escape from an endosome and deliver a nucleic acid into a cytoplasm, it is important to set the Liposomal pKa to a value preferable for the escape from the endosome. By adjusting the Liposomal pKa to fall within the above ranges, a nucleic acid can be efficiently delivered into a cytoplasm. The Liposomal pKa can be appropriately adjusted by selecting the cationic lipid (1) of the present invention used as the constituent component of a lipid membrane structure.

The nucleic acid-introducing agent of the present invention encapsulating a nucleic acid is brought into contact with cells to introduce the nucleic acid into the cells. The kind of the cell is not particularly limited, and a prokaryotic or eukaryotic cell can be used. The cell is preferably a eukaryote cell. The kind of the eukaryote is not particularly limited and for example, vertebrates such as mammals including human (e.g., human, monkey, mouse, rat, hamster, bovine, and the like), birds (e.g., chicken, ostrich, and the like), *amphibia* (e.g., frog and the like), fishes (e.g., zebrafish, rice-fish, and the like) and the like, invertebrates such as insects (silk moth, moth, *Drosophila*, and the like), and the like, plants, microorganisms (e.g., yeasts), and the like can be mentioned. The cell is more preferably an animal or plant cell, further preferably a mammalian cell. The cell may be a culture cell line including a cancer cell, or a cell isolated from an individual or tissue, or a cell of a tissue or tissue piece. The cell may be an adherent cell or a non-adherent cell.

The step of contacting the nucleic acid-introducing agent of the present invention encapsulating a nucleic acid with a cell in vitro is specifically described below.

Cells are suspended in a suitable medium several days before contact with a nucleic acid-introducing agent encapsulating a nucleic acid, and cultured under appropriate conditions. At the time of contact with the nucleic acid-introducing agent, the cells may or may not be in a proliferative phase.

The culture medium at the time of contact of the cell and the nucleic acid-introducing agent encapsulating a nucleic acid of the present invention may be a serum-containing medium or a serum-free medium. The serum concentration of the medium is preferably not more than 30 wt %, more preferably not more than 20 wt %. When the medium contains excess proteins such as serum and the like, the contact between the nucleic acid-introducing agent and the cell may be inhibited.

The cell density at the time of contact of the cell and the nucleic acid-introducing agent of the present invention encapsulating a nucleic acid is not particularly limited, and can be appropriately determined in consideration of the kind of the cell and the like. It is generally within the range of $1\times10^4$ to $1\times10^7$ cells/mL.

For example, a dispersion of the aforementioned nucleic acid-introducing agent of the present invention encapsulating a nucleic acid is added to cells. The amount of the dispersion to be added is not particularly limited, and can be appropriately determined in consideration of the cell number and the like. The concentration of the nucleic acid-introducing agent in the dispersion when contacting cells is not particularly limited as long as the desired introduction of the nucleic acid into the cells can be achieved. The lipid concentration in the dispersion is generally 1 to 100 nmol/ml, preferably 10 to 50 nmol/ml, and the concentration of the nucleic acid in the dispersion is generally 0.01 to 100 μg/ml, preferably 0.1 to 10 μg/ml.

After the aforementioned dispersion is added to cells, the cells are cultured. The temperature, humidity and $CO_2$ concentration during culturing are appropriately determined in consideration of the kind of the cell. When the cell is derived from a mammal, generally, the temperature is about 37° C., the relative humidity is about 95%, and the $CO_2$ concentration is about 5 vol %. While the culture time can also be appropriately determined in consideration of the conditions such as the kind of the cell and the like, it is generally a range of 0.1 to 76 hr, preferably a range of 0.2 to 24 hr, more preferably a range of 0.5 to 12 hr. When the above-mentioned culture time is too short, the nucleic acid is not sufficiently introduced into the cells, and when the culture time is too long, the cells may become weak.

By the above-mentioned culture, a nucleic acid is introduced into cells. The culture is further continued preferably by exchanging the medium with a fresh medium, or adding a fresh medium to the medium. When the cell is a mammal-derived cell, the fresh medium preferably contains a serum or nutrition factor.

A nucleic acid can be introduced into cells not only outside the body (in vitro) but also in the body (in vivo) by using the nucleic acid-introducing agent of the present invention encapsulating a nucleic acid. That is, by administration of the nucleic acid-introducing agent to a subject, the nucleic acid-introducing agent reaches and contacts with the target cells, and a nucleic acid is introduced into the cells in vivo. The subject to which the nucleic acid-introducing agent can be administered is not particularly limited and, for example, vertebrates such as mammals (e.g., human, monkey, mouse, rat, hamster, bovine, and the like), birds (e.g., chicken, ostrich, and the like), *amphibia* (e.g., frog and the like), fishes (e.g., zebrafish, rice-fish, and the like), and the like, invertebrates such as insects (e.g., silk moth, moth, *Drosophila*, and the like) and the like, plants, and the like can be mentioned. The subject of administration of the nucleic acid-introducing agent is preferably human or other mammals.

The kind of the target cell is not particularly limited, and a nucleic acid can be introduced into cells in various tissues (e.g., liver, kidney, pancreas, lung, spleen, heart, blood, muscle, bone, brain, stomach, small intestine, large intestine, skin, adipose tissue, lymph node, tumor, and the like) by using the nucleic acid-introducing agent of the present invention.

The administration method of the nucleic acid-introducing agent of the present invention encapsulating a nucleic acid to a target (e.g., vertebrate, invertebrate and the like) is not particularly limited as long as the nucleic acid-introducing agent of the present invention reaches and contacts with the target cells, and the nucleic acid can be introduced into the cell, and an administration method known per se (e.g., oral administration, parenteral administration (e.g., intravenous administration, intramuscular administration, topical administration, transdermal administration, subcutaneous administration, intraperitoneal administration, spray, and the like), and the like) can be appropriately selected in consideration of the kind of the nucleic acid to be introduced, the kind and the site of the target cell, and the like. The dose of the nucleic acid-introducing agent is not particularly limited as long as the introduction of the nucleic acid into the cells can be achieved, and can be appropriately selected in consideration of the kind of the subject of administration, the administration method, the kind of the nucleic acid to be introduced, the kind and the site of the target cell, and the like.

The cationic lipid (1) and lipid membrane structure of the present invention can also be used for introducing a compound other than nucleic acids into a cell.

A nucleic acid-introducing agent containing the cationic lipid (1) or lipid membrane structure of the present invention can be formulated according to a conventional method.

When the nucleic acid-introducing agent of the present invention is provided as a reagent for studies, the nucleic acid-introducing agent of the present invention may be provided as a sterile solution or dispersion containing the cationic lipid (1) or lipid membrane structure of the present invention, and water or other physiologically acceptable solvent (e.g., water-soluble solvent (e.g., malic acid buffer and the like), organic solvent (e.g., ethanol, methanol, DMSO, tert-butanol, and the like), or a mixture of aqueous solvent and organic solvent), or it may be provided as a nucleic acid-introducing agent free of solvent. The nucleic acid-introducing agent of the present invention may appropriately contain physiologically acceptable additives (e.g., excipient, vehicle, preservative, stabilizer, binder, and the like), which is known per se.

When the nucleic acid-introducing agent of the present invention is provide as a medicament, the nucleic acid-introducing agent of the present invention may be provided as an oral preparation (e.g., tablet, capsule, and the like) or a parenteral agent (e.g., injection, spray, and the like), which is obtained by mixing the cationic lipid (1) or lipid membrane structure of the present invention with pharmaceutically acceptable known additives (e.g., carrier, flavor, excipient, vehicle, preservative, stabilizer, binder, and the like), or may be provided as a nucleic acid-introducing agent free of known additives. The nucleic acid-introducing agent of the present invention as a medicament is preferably a parenteral agent, more preferably an injection. In addition, the nucleic acid-introducing agent of the present invention may be a preparation for adults or a preparation for children.

The nucleic acid-introducing agent of the present invention can also be provided in the form of a kit. The kit can contain, in addition to the cationic lipid (1) or lipid membrane structure of the present invention, a reagent used for the introduction of a nucleic acid. In one embodiment, the nucleic acid-introducing agent (or kit) of the present invention further contains a polycation (e.g., protamine). Using the nucleic acid-introducing agent (or kit) of the present invention in this embodiment, an electrostatic complex of a nucleic acid and a polycation (e.g., protamine) can be encapsulated in the lipid membrane structure of the present invention, whereby the nucleic acid can be more effectively introduced into cells.

EXAMPLE

The Examples of the present invention are described in further detail in the following, but the present invention is not limited in any way by the Examples.

The abbreviations used in the description of Examples each mean the following.

DCM: dichloromethane
THF: tetrahydrofuran
DHP: 3,4-dihydro-2H-pyran
PPTS: pyridinium p-toluenesulfonate
DBU: diazabicycloundecene
DMAP: 4-dimethylaminopyridine
EDC: 1-(3-dimethylaminopropyl)-3-ethylcarbodiimide-hydrochloride
Fmoc: 9-fluorenylmethyloxycarbonyl group
mRNA: messenger RNA
Chol: cholesterol
DMG-PEG2k: 1,2-di myristoyl-sn-glycerol-3-methoxy-polyethylene glycol (weight average molecular weight of polyethylene glycol chain: 2000)
DOPC: 1,2-dioleoyl-sn-glycerol-3-phosphocholine
PBS: phosphate buffered saline
MES: 2-morpholinoethanesulfonic acid
TNS: sodium 6-(p-toluidino)-2-naphthalenesulfonate
TEA: triethylamine Tables 3 and 4 show the names and structures of the cationic lipids produced in the following Examples.

TABLE 3

| | name of cationic lipid | structure |
|---|---|---|
| Example 1 | O-Ph-cys-C2-DMA | 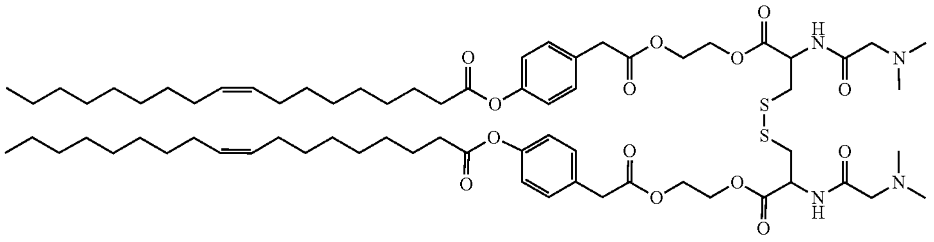 [SMILES: CCCCCCCC/C=C\CCCCCCCC(=O)Oc1ccc(CC(=O)OCCOC(=O)C(CSSCC(NC(=O)CN(C)C)C(=O)OCCOC(=O)Cc2ccc(OC(=O)CCCCCCC/C=C\CCCCCCCC)cc2)NC(=O)CN(C)C)cc1] |

TABLE 3-continued
| | name of cationic lipid | structure |
|---|---|---|
| Example 2 | O-Ph-cys-C2-EMA | 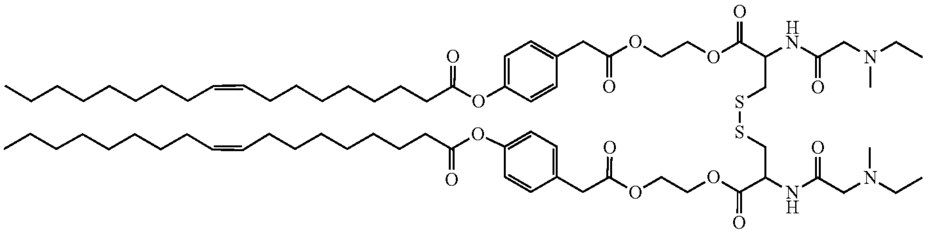 [SMILES: CCCCCCCC/C=C\CCCCCCCC(=O)Oc1ccc(CC(=O)OCCOC(=O)C(CSSCC(NC(=O)CN(C)CC)C(=O)OCCOC(=O)Cc2ccc(OC(=O)CCCCCCC/C=C\CCCCCCCC)cc2)NC(=O)CN(C)CC)cc1] |
| Example 3 | O-Ph-cys-C2-MPA | 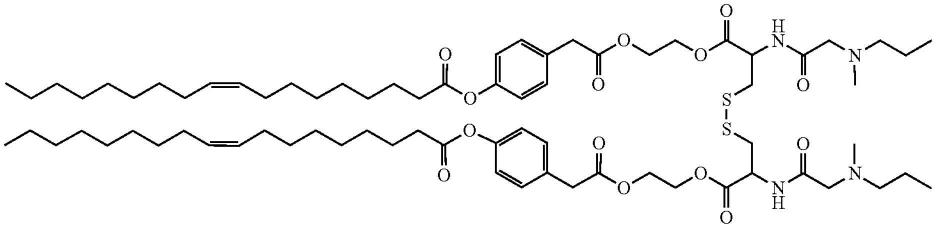 [SMILES: CCCCCCCC/C=C\CCCCCCCC(=O)Oc1ccc(CC(=O)OCCOC(=O)C(CSSCC(NC(=O)CN(C)CCC)C(=O)OCCOC(=O)Cc2ccc(OC(=O)CCCCCCC/C=C\CCCCCCCC)cc2)NC(=O)CN(C)CCC)cc1] |
| Example 4 | O-Ph-cys-C2-DEA | 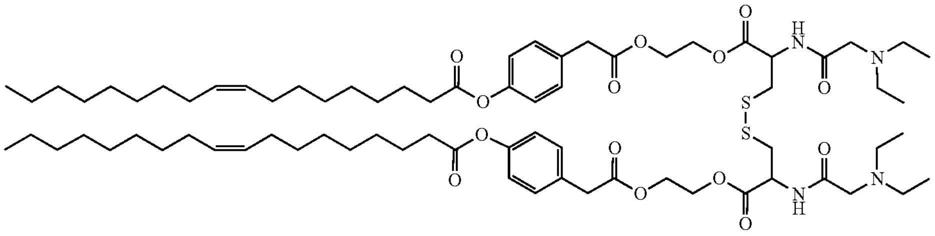 [SMILES: CCCCCCCC/C=C\CCCCCCCC(=O)Oc1ccc(CC(=O)OCCOC(=O)C(CSSCC(NC(=O)CN(CC)CC)C(=O)OCCOC(=O)Cc2ccc(OC(=O)CCCCCCC/C=C\CCCCCCCC)cc2)NC(=O)CN(CC)CC)cc1] |
| Example 5 | O-Ph-cys-C2-DPA | 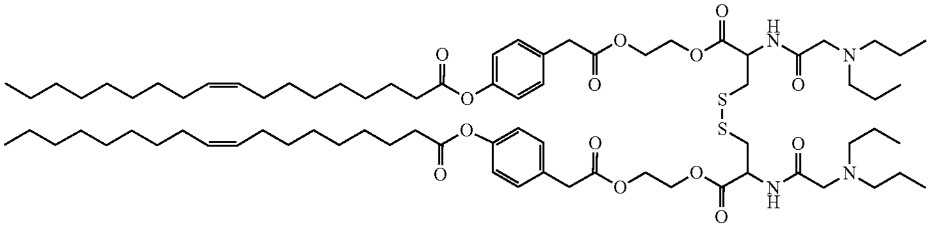 [SMILES: CCCCCCCC/C=C\CCCCCCCC(=O)Oc1ccc(CC(=O)OCCOC(=O)C(CSSCC(NC(=O)CN(CCC)CCC)C(=O)OCCOC(=O)Cc2ccc(OC(=O)CCCCCCC/C=C\CCCCCCCC)cc2)NC(=O)CN(CCC)CCC)cc1] |
TABLE 4
| | name of cationic lipid | structure |
|---|---|---|
| Example 6 | O-Ph-cys-C2-DIA | 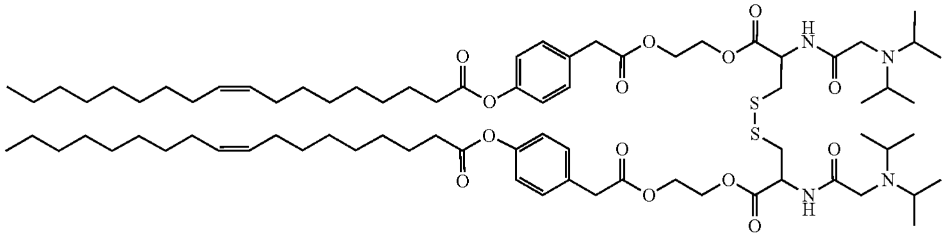 [SMILES: CCCCCCCC/C=C\CCCCCCCC(=O)Oc1ccc(CC(=O)OCCOC(=O)C(CSSCC(NC(=O)CN(C(C)C)C(C)C)C(=O)OCCOC(=O)Cc2ccc(OC(=O)CCCCCCC/C=C\CCCCCCCC)cc2)NC(=O)CN(C(C)C)C(C)C)cc1] |

TABLE 4-continued
| | name of cationic lipid | structure |
|---|---|---|
| Example 7 | O-Ph-cys-C2-Pip | 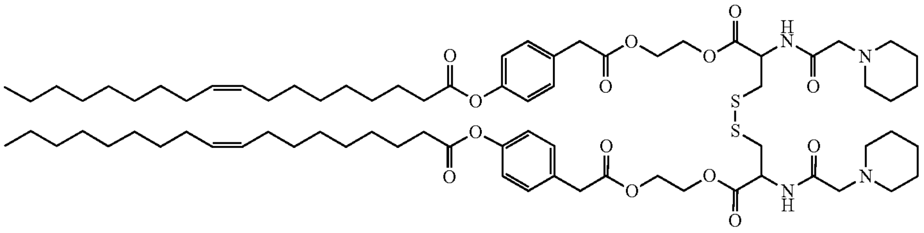 [SMILES: CCCCCCCC/C=C\CCCCCCCC(=O)Oc1ccc(CC(=O)OCCOC(=O)C(CSSCC(NC(=O)CN2CCCCC2)C(=O)OCCOC(=O)Cc2ccc(OC(=O)CCCCCCC/C=C\CCCCCCCC)cc2)NC(=O)CN2CCCCC2)cc1] |
| Example 8 | E-Ph-cys-C2-DMA | 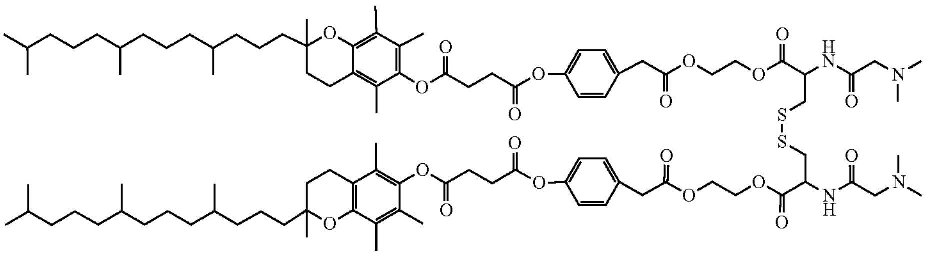 [SMILES: Cc1c(C)c2c(c(C)c1OC(=O)CCC(=O)Oc1ccc(CC(=O)OCCOC(=O)C(CSSCC(NC(=O)CN(C)C)C(=O)OCCOC(=O)Cc3ccc(OC(=O)CCC(=O)Oc4c(C)c(C)c5c(c4C)CCC(C)(CCCC(C)CCCC(C)CCCC(C)C)O5)cc3)NC(=O)CN(C)C)cc1)CCC(C)(CCCC(C)CCCC(C)CCCC(C)C)O2] |
| Example 9 | O-Ph-cys-C4-DMA | 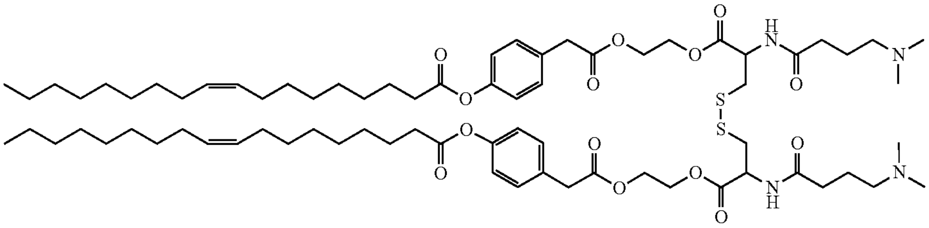 [SMILES: CCCCCCCC/C=C\CCCCCCCC(=O)Oc1ccc(CC(=O)OCCOC(=O)C(CSSCC(NC(=O)CCCN(C)C)C(=O)OCCOC(=O)Cc2ccc(OC(=O)CCCCCCC/C=C\CCCCCCCC)cc2)NC(=O)CCCN(C)C)cc1] |
| Example 10 | O-Ph-cys-DMA | 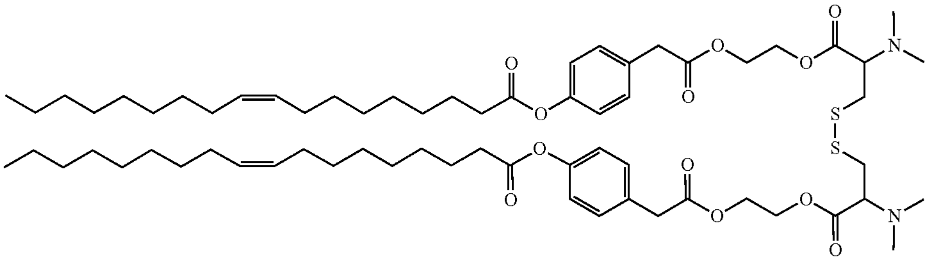 [SMILES: CCCCCCCC/C=C\CCCCCCCC(=O)Oc1ccc(CC(=O)OCCOC(=O)C(CSSCC(C(=O)OCCOC(=O)Cc2ccc(OC(=O)CCCCCCC/C=C\CCCCCCCC)cc2)N(C)C)N(C)C)cc1] |
[Example 1] Synthesis of O-Ph-cys-C2-DMA
While O-Ph-cys-C2-DMA was produced by the following synthetic pathway, the present invention is not limited to such synthetic pathway.
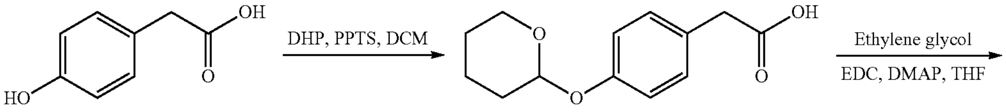
intermediate 1

-continued
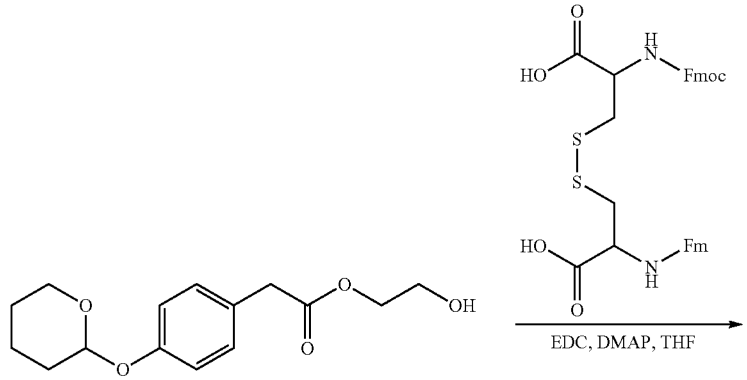
inter-
mediate 2
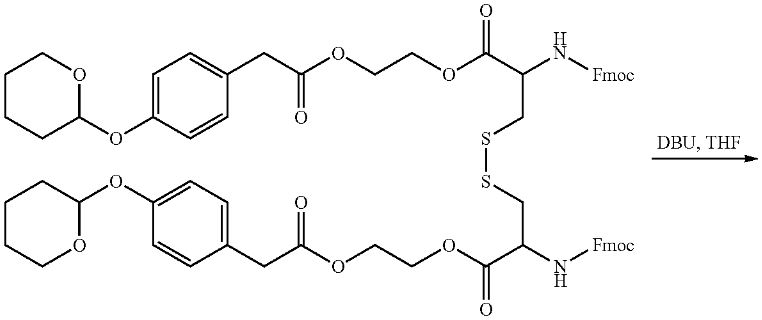
inter-
mediate 3
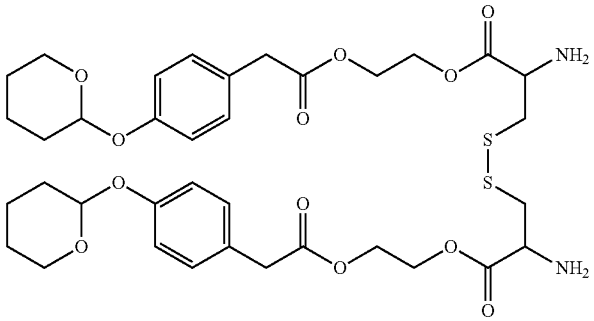
inter-
mediate 4
inter-
mediate 4
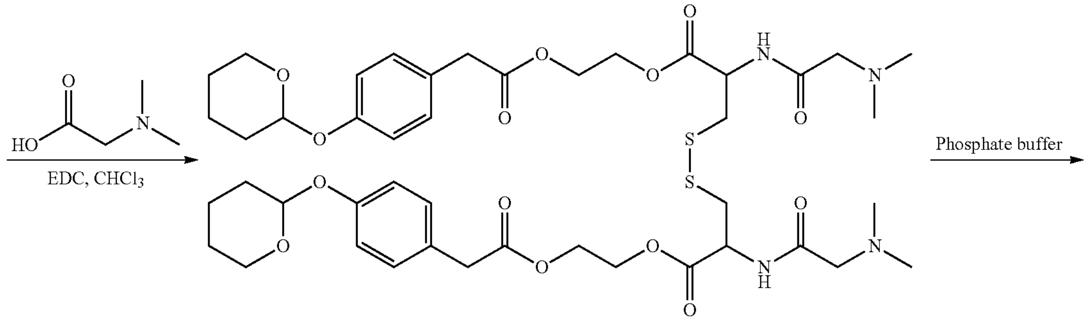
inter-
mediate 5

-continued

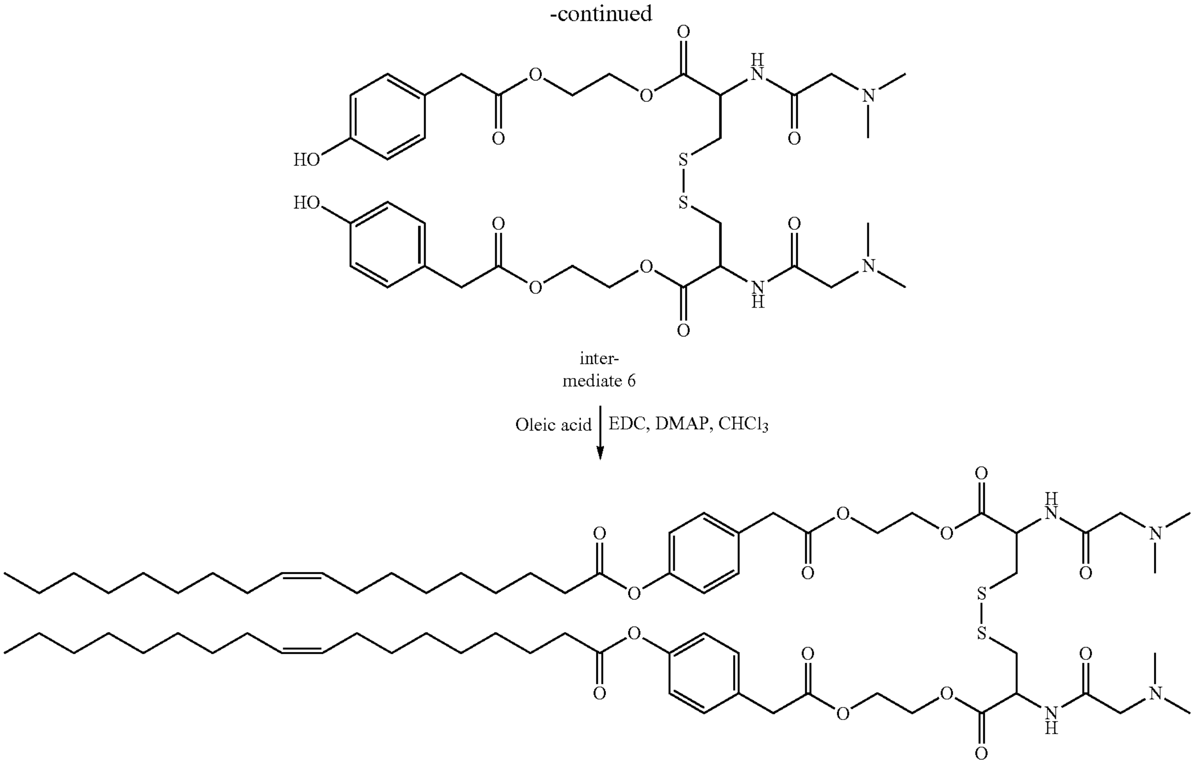

intermediate 6

O-Ph-cys-C2-DMA

Synthesis of Intermediate 1

4-Hydroxyphenylacetic acid (manufactured by KANTO CHEMICAL CO., INC.) (75.0 g, 493 mmol) and pyridinium p-toluenesulfonate (manufactured by KANTO CHEMICAL CO., INC.) (12.4 g, 49.3 mmol) were dissolved in dichloromethane (400 g) at room temperature, and the obtained solution was cooled to 10 to 20° C. A solution of DHP (manufactured by FUJIFILM Wako Pure Chemical Corporation) (207 g, 2.46 mol) in dichloromethane (100 g) was added dropwise thereto, and the mixture was reacted at 25° C. for 2 hr. The reaction solution was cooled to 10 to 20° C. and DMAP (manufactured by KOEI CHEMICAL COMPANY, LIMITED) (30.1 g, 246 mmol) was added to quench the reaction. To the solution after quenching was added 2-propanol (590 g), and the mixture was stirred at cooled to 10 to 20° C. After cooling, to the solution was added dropwise a mixture of 400 g/L sodium hydroxide aqueous solution (98.8 g) and ion exchanged water (307 g), and the mixture was reacted at 25° C. for 2 hr. The reaction solution was concentrated by an evaporator to evaporate dichloromethane and 2-propanol. The obtained concentrate was washed twice with chloroform (750 g), and 6N hydrochloric acid was added to give a mixture at pH 5.0. The obtained mixture was extracted twice with chloroform (750 g), and the organic layer was dehydrated by adding sodium sulfate (75.0 g). Sodium sulfate was removed by filtration, and the filtrate was concentrated by an evaporator to give 98.2 g of intermediate 1.

Synthesis of Intermediate 2

Intermediate 1 (25.0 g, 106 mmol) and DMAP (2.60 g, 21.3 mmol) were dissolved in THF (225 g) at room temperature, and dehydrated ethylene glycol (manufactured by FUJIFILM Wako Pure Chemical Corporation) (222 g, 3.58 mol) was added to the obtained solution. To the obtained mixture was added EDC (manufactured by Tokyo Chemical Industry Co., Ltd.) (40.6 g, 212 mmol) and the mixture was reacted at 25° C. for 2 hr. The reaction solution was concentrated by an evaporator to evaporate THF. The obtained concentrate was extracted with chloroform (250 g), and the organic layer was washed twice with 0.5 M phosphate buffer (pH 3.0) (250 g) and once with 20 wt % brine (250 g), and dehydrated by adding sodium sulfate (50 g). Sodium sulfate was removed by filtration, and the filtrate was concentrated by an evaporator to give 28.4 g of intermediate 2.

Synthesis of Intermediate 3

Intermediate 2 (16.4 g, 58.5 mmol), N,N'-bis(9-fluorenylmethyloxycarbonyl)-L-cystine (manufactured by WATANABE CHEMICAL INDUSTRIES, LTD.) (20 g, 29.2 mmol), and DMAP (1.43 g, 11.7 mmol) were dissolved in THE (100 g) at room temperature. To the obtained solution was added EDC (16.8 g, 87.6 mmol) and the mixture was reacted at 25° C. for 2 hr. The reaction solution was extracted with chloroform (250 g), and the organic layer was washed twice with 0.5 M phosphate buffer (pH 3.0) (250 g) and once with 20 wt % brine (250 g), and dehydrated by adding sodium sulfate (40 g). Sodium sulfate was removed by filtration, and the filtrate was concentrated by an evaporator to give 31.5 g of intermediate 3.

Synthesis of Intermediate 4

Intermediate 3 (15.0 g, 12.4 mmol) was dissolved in THE (333 g) at room temperature. To the obtained solution was added DBU (manufactured by Tokyo Chemical Industry Co., Ltd.) (1.42 g, 9.33 mmol), and the mixture was reacted at 25° C. for 1 hr. The reaction solution was diluted with 150 mM phosphate buffer (pH 3.0) (750 g) and washed twice with hexane (487 g). The diluted solution after washing was extracted twice with chloroform (1120 g), and the organic layer was washed with 20 wt % brine (750 g). The organic layer after washing was dehydrated by adding sodium sulfate (30.0 g). Sodium sulfate was removed by filtration, and the filtrate was concentrated by an evaporator to give 6.30 g of intermediate 4.

Synthesis of Intermediate 5

Intermediate 4 (600 mg, 0.784 mmol) and N,N-dimethylglycine (manufactured by Tokyo Chemical Industry Co., Ltd.) (194 mg, 1.88 mmol) were dissolved in chloroform (89.0 g) at room temperature. EDC (601 mg, 3.14 mmol) was added, and the mixture was reacted at 25° C. for 2 hr. The reaction solution was washed twice with 0.5 M phosphate buffer (pH 4.0) (60 g), once with 7 wt % sodium bicarbonate water (60.0 g), and once with 20 wt % brine (60 g), and dehydrated by adding sodium sulfate (7.00 g). Sodium sulfate was removed by filtration, and the filtrate was concentrated by an evaporator to give 695 mg of intermediate 5.

Synthesis of Intermediate 6

To intermediate 5 (680 mg, 0.727 mmol) was added 0.5 M phosphate buffer (pH 2.0) (68.0 g), and the mixture was reacted at 25° C. for 2 hr. The reaction solution was washed with chloroform (100 g). The aqueous layer after washing was adjusted to pH 6.0 by adding 400 g/L sodium hydroxide aqueous solution. The aqueous layer after pH adjustment was extracted twice with chloroform (100 g). The organic layer was dehydrated by adding sodium sulfate (1.36 g). Sodium sulfate was removed by filtration, and the filtrate was concentrated by an evaporator to give 278 mg of intermediate 6.

Synthesis of O-Ph-cys-C2-DMA

Intermediate 6 (250 mg, 0.326 mmol), oleic acid (manufactured by NOF CORPORATION) (184 mg, 0.652 mmol), and DMAP (15.9 mg, 0.130 mmol) were dissolved in chloroform (17.6 g) at room temperature. To the obtained solution was added EDC (187 mg, 0.976 mmol), and the mixture was reacted at 25° C. for 2 hr. The reaction solution was washed twice with 20 wt % brine (12.0 g), and dehydrated by adding sodium sulfate (500 mg). Sodium sulfate was removed by filtration, and the filtrate was concentrated by an evaporator to give 369 mg of a crude product. The obtained crude product was subjected to column purification to give 222 mg of O-Ph-cys-C2-DMA.

<$^1$H-NMR of O-Ph-cys-C2-DMA (600 MHz, $CDCl_3$)>

δ: 0.86-0.90 (t, 6H), 1.22-1.42 (m, 40H), 1.72-1.77 (m, 4H), 1.99-2.05 (m, 8H), 2.32 (s, 12H), 2.52-2.56 (t, 4H), 2.90-3.03 (m, 4H), 3.09-3.43 (m, 4H), 3.63 (s, 4H), 4.30-4.37 (m, 8H), 4.88-4.97 (m, 2H), 5.32-5.38 (m, 4H), 7.02-7.05 (m, 4H), 7.27-7.30 (m, 4H), 7.81-7.88 (d, 2H)

[Example 2] Synthesis of O-Ph-cys-C2-EMA

Synthesis of N-ethyl-N-methylglycine

N-ethylmethylamine (manufactured by Tokyo Chemical Industry Co., Ltd.) (8.50 g, 144 mmol) was dissolved in THF (45 g) at ordinary temperature, and the mixture was cooled to 10° C. or below. A solution of bromoacetic acid (manufactured by Tokyo Chemical Industry Co., Ltd.) (2.00 g, 14.4 mmol) in THE (9.00 g) was added dropwise thereto, and the mixture was reacted at 25° C. for 2 hr. White precipitate was removed by filtration, and the filtrate was concentrated by an evaporator to remove THF. To the obtained concentrate was added ion exchanged water (10.0 g) to prepare a solution. The pH thereof was adjusted to 12.0 with 400 g/L sodium hydroxide aqueous solution. The solution with the adjusted pH was washed 3 times with chloroform (15.0 g), the aqueous layer after washing was neutralized to pH 7.0 with 6N hydrochloric acid, and the aqueous layer after neutralization was concentrated by an evaporator. To the obtained residue was added acetonitrile (50.0 g) to prepare a solution, and the solution was dehydrated by adding sodium sulfate (4.00 g). Sodium sulfate was removed by filtration, and the filtrate was concentrated by an evaporator to give 1.35 g of N-ethyl-N-methylglycine represented by the following formula.

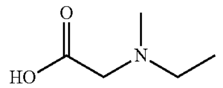

Synthesis of O-Ph-cys-C2-EMA

Using intermediate 4 and N-ethyl-N-methylglycine, O-Ph-cys-C2-EMA was synthesized by the same synthetic pathway as in Example 1.

<$^1$H-NMR of O-Ph-cys-C2-EMA (600 MHz, $CDCl_3$)>

δ: 0.86-0.90 (t, 6H), 1.05-1.09 (t, 6H), 1.22-1.42 (m, 40H), 1.72-1.77 (m, 4H), 1.99-2.05 (m, 8H), 2.31 (s, 6H), 2.49-2.56 (m, 8H), 2.96-3.07 (m, 4H), 3.10-3.43 (m, 4H), 3.63 (s, 4H), 4.30-4.37 (m, 8H), 4.88-4.97 (m, 2H), 5.32-5.38 (m, 4H), 7.02-7.05 (m, 4H), 7.27-7.30 (m, 4H), 7.94-8.01 (d, 2H)

[Example 3] Synthesis of O-Ph-cys-C2-MPA

Synthesis of N-methyl-N-propylglycine

In the same manner as in Example 2 except that N-methylpropylamine (manufactured by Tokyo Chemical Industry Co., Ltd.) was used, N-methyl-N-propylglycine represented by the following formula was synthesized.

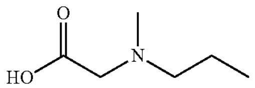

Synthesis of O-Ph-cys-C2-MPA

Using intermediate 4 and N-methyl-N-propylglycine, O-Ph-cys-C2-MPA was synthesized by the same synthetic pathway as in Example 1.

<$^1$H-NMR of O-Ph-cys-C2-MPA (600 MHz, $CDCl_3$)>

δ: 0.86-0.93 (m, 12H), 1.22-1.42 (m, 40H), 1.47-1.52 (m, 4H), 1.72-1.77 (m, 4H), 1.99-2.05 (m, 8H), 2.30 (s, 6H), 2.38-2.42 (m, 4H), 2.52-2.56 (t, 4H), 2.96-3.07 (m, 4H), 3.11-3.43 (m, 4H), 3.63 (s, 4H), 4.30-4.37 (m, 8H), 4.88-

4.97 (m, 2H), 5.32-5.38 (m, 4H), 7.02-7.05 (m, 4H), 7.27-7.30 (m, 4H), 7.94-8.01 (d, 2H)

[Example 4] Synthesis of O-Ph-cys-C2-DEA

Using intermediate 4 and N,N-diethylglycine sodium salt (manufactured by Tokyo Chemical Industry Co., Ltd.), O-Ph-cys-C2-DEA was synthesized by the same synthetic pathway as in Example 1.

<$^1$H-NMR of O-Ph-cys-C2-DEA (600 MHz, $CDCl_3$)>

δ: 0.86-0.90 (t, 6H), 1.03-1.06 (t, 12H), 1.22-1.42 (m, 40H), 1.72-1.77 (m, 4H), 1.99-2.05 (m, 8H), 2.52-2.61 (m, 12H), 3.00-3.43 (m, 8H), 3.63 (s, 4H), 4.30-4.37 (m, 8H), 4.88-4.97 (m, 2H), 5.32-5.38 (m, 4H), 7.02-7.05 (m, 4H), 7.27-7.30 (m, 4H), 8.13-8.20 (d, 2H)

[Example 5] Synthesis of O-Ph-cys-C2-DPA

N,N-dipropylglycine

In the same manner as in Example 2 except that dipropylamine (manufactured by Tokyo Chemical Industry Co., Ltd.) was used, N,N-dipropylglycine represented by the following formula was synthesized.

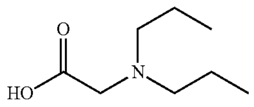

Synthesis of O-Ph-cys-C2-DPA

Using intermediate 4 and N,N-dipropylglycine, O-Ph-cys-C2-DPA was synthesized by the same synthetic pathway as in Example 1.

<$^1$H-NMR of O-Ph-cys-C2-DPA (600 MHz, $CDCl_3$)>

δ 0.86-0.92 (m, 18H), 1.22-1.51 (m, 48H), 1.72-1.77 (m, 4H), 1.99-2.05 (m, 8H), 2.43-2.46 (t, 8H), 2.52-2.55 (t, 4H), 3.02-3.43 (m, 8H), 3.63 (s, 4H), 4.30-4.37 (m, 8H), 4.86-4.95 (m, 2H), 5.32-5.38 (m, 4H), 7.02-7.05 (m, 4H), 7.27-7.30 (m, 4H), 8.09-8.16 (d, 2H)

[Example 6] Synthesis of O-Ph-cys-C2-DIA

Synthesis of N,N-diisopropylglycine

In the same manner as in Example 2 except that diisopropylamine (manufactured by Tokyo Chemical Industry Co., Ltd.) was used, N,N-diisopropylglycine represented by the following formula was synthesized.

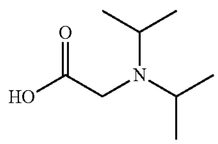

Synthesis of <O-Ph-cys-C2-DIA>

Using intermediate 4 and N,N-diisopropylglycine, O-Ph-cys-C2-DIA was synthesized by the same synthetic pathway as in Example 1.

<$^1$H-NMR of O-Ph-cys-C2-DIA (600 MHz, $CDCl_3$)>

δ: 0.86-0.90 (t, 6H), 1.02 (s, 24H), 1.22-1.42 (m, 40H), 1.72-1.77 (m, 4H), 1.99-2.05 (m, 8H), 2.52-2.60 (m, 8H), 3.02-3.43 (m, 8H), 3.63 (s, 4H), 4.30-4.37 (m, 8H), 4.86-4.95 (m, 2H), 5.32-5.38 (m, 4H), 7.02-7.05 (m, 4H), 7.27-7.30 (m, 4H), 8.09-8.16 (d, 2H)

[Example 7] Synthesis of O-Ph-cys-C2-Pip

Synthesis of 2-(1-piperidyl)acetic Acid

In the same manner as in Example 2 except that piperidine (manufactured by FUJIFILM Wako Pure Chemical Corporation) was used, 2-(1-piperidyl)acetic acid represented by the following formula was synthesized.

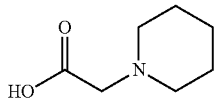

Synthesis of O-Ph-cys-C2-Pip

Using intermediate 4 and 2-(1-piperidyl)acetic acid, 0-Ph-cys-C2-Pip was synthesized by the same synthetic pathway as in Example 1.

<$^1$H-NMR of O-Ph-cys-C2-Pip (600 MHz, $CDCl_3$)>

δ: 0.86-0.90 (t, 6H), 1.22-1.48 (m, 44H), 1.60-1.63 (m, 8H), 1.72-1.77 (m, 4H), 1.99-2.05 (m, 8H), 2.43-2.56 (m, 12H), 2.94-3.02 (m, 4H), 3.13-3.43 (m, 4H), 3.63 (s, 4H), 4.30-4.37 (m, 8H), 4.88-4.97 (m, 2H), 5.32-5.38 (m, 4H), 7.02-7.05 (m, 4H), 7.27-7.30 (m, 4H), 8.02-8.09 (d, 2H)

[Example 8] Synthesis of E-Ph-cys-C2-DMA

Using intermediate 6 and D-a-tocopherol succinate (manufactured by Tokyo Chemical Industry Co., Ltd.), E-Ph-cys-C2-DMA was synthesized by the same synthetic pathway as in Example 1.

<$^1$H-NMR of E-Ph-cys-C2-DMA (600 MHz, $CDCl_3$)>

δ: 0.83-0.88 (m, 24H), 1.00-1.81 (m, 52H), 1.98 (s, 6H), 2.01 (s, 6H), 2.08 (s, 6H), 2.32 (s, 12H), 2.55-2.60 (t, 4H), 2.80-2.83 (m, 4H), 2.90-3.03 (m, 8H), 3.09-3.43 (m, 4H), 3.63 (s, 4H), 4.30-4.37 (m, 8H), 4.88-4.97 (m, 2H), 7.02-7.05 (m, 4H), 7.27-7.30 (m, 4H), 7.81-7.88 (d, 2H)

[Example 9] Synthesis of O-Ph-cys-C4-DMA

Using intermediate 4 and 4-(dimethylamino)butyric acid hydrochloride (manufactured by SIGMA-ALDRICH), O-Ph-cys-C4-DMA was synthesized by the same synthetic pathway as in Example 1.

<$^1$H-NMR of O-Ph-cys-C4-DMA (600 MHz, $CDCl_3$)>

δ: 0.86-0.90 (t, 6H), 1.22-1.42 (m, 40H), 1.72-1.83 (m, 8H), 1.99-2.05 (m, 8H), 2.20-2.40 (m, 20H), 2.52-2.56 (t, 4H), 3.02-3.39 (m, 4H), 3.63 (s, 4H), 4.30-4.37 (m, 8H), 4.80-4.89 (m, 2H), 5.32-5.38 (m, 4H), 7.02-7.05 (m, 4H), 7.27-7.30 (m, 4H), 7.68-7.78 (d, 2H)

[Example 10] Synthesis of O-Ph-cys-DMA

While O-Ph-cys-DMA was produced by the following synthetic pathway, the present invention is not limited to such synthetic pathway.

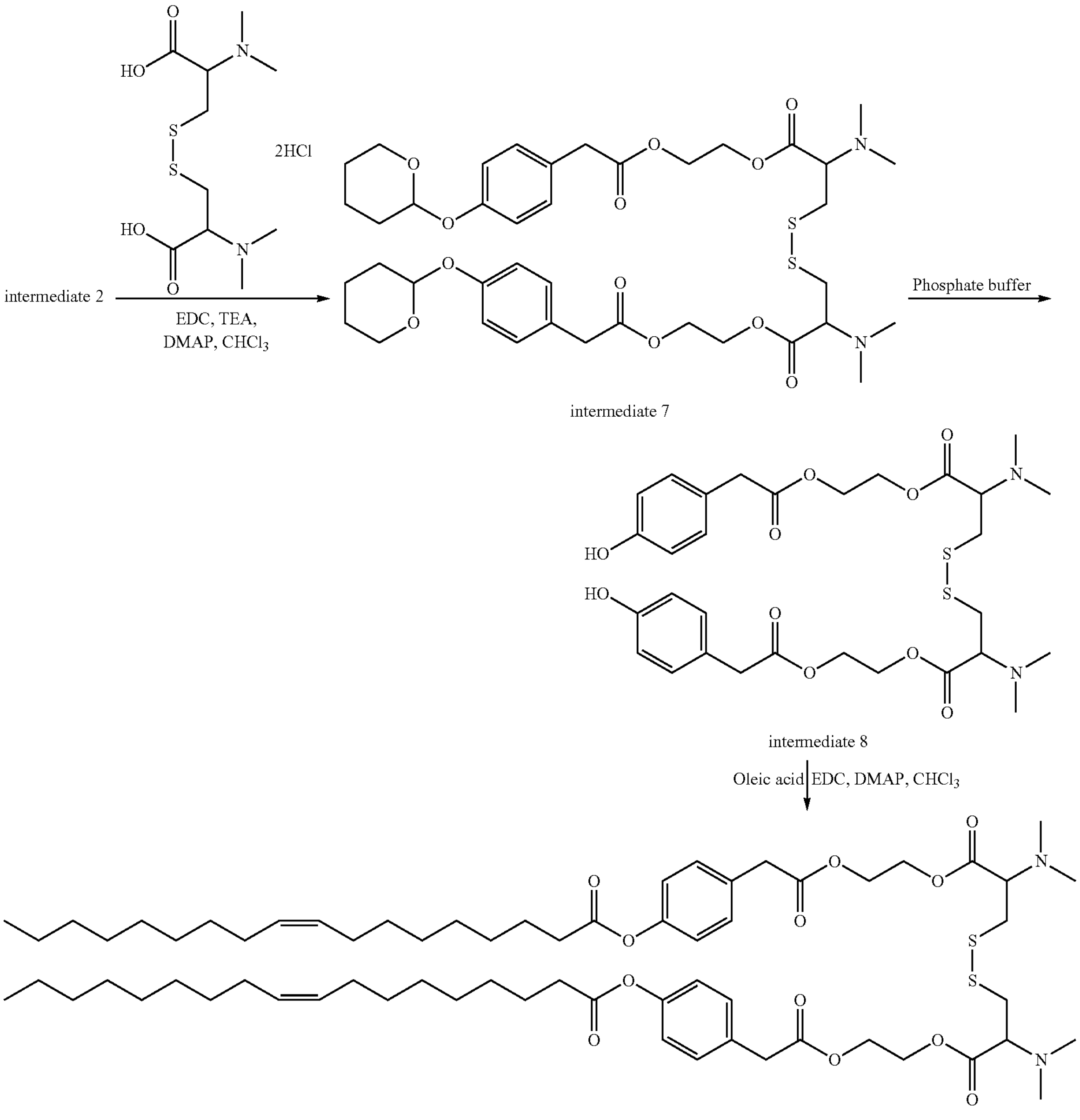

intermediate 2 intermediate 7 intermediate 8

O-Ph-cys-DMA

Synthesis of Intermediate 7

Intermediate 2 (757 mg, 2.70 mmol), N,N,N',N'-tetramethyl-L-cystine dihydrochloride (manufactured by Toronto Research Chemicals) (500 mg, 1.35 mmol), triethylamine (manufactured by KANTO CHEMICAL CO., INC.) (820 mg, 8.10 mmol), and DMAP (198 mg, 1.62 mmol) were dissolve chloroform (15.0 g) at room temperature. To the obtained residue was added EDC (1.04 g, 5.40 mmol), and the mixture was reacted at 25° C. for 2 hr. The reaction solution was washed twice with 0.5 M phosphate buffer (pH 3.0) (10.0 g) and once with 7 wt % brine (10.0 g), and dehydrated by adding sodium sulfate (1.00 g). Sodium sulfate was removed by filtration, and the filtrate was concentrated by an evaporator to give 960 mg of intermediate 7.

Synthesis of Intermediate 8

To intermediate 7 (900 mg, 1.10 mmol) was added 0.5 M phosphate buffer (pH 2.0) (90.0 g), and the mixture was reacted at 25° C. for 2 hr. The reaction solution was washed with chloroform (130 g). The aqueous layer after washing was adjusted to pH 6.0 by adding 400 g/L sodium hydroxide aqueous solution, and the mixture was extracted twice with chloroform (130 g). The organic layer was dehydrated by adding sodium sulfate (1.80 g). Sodium sulfate was removed by filtration, and the filtrate was concentrated by an evaporator to give 359 mg of intermediate 8.

Synthesis of O-Ph-cys-DMA

Intermediate 8 (340 mg, 0.521 mmol), oleic acid (294 mg, 1.04 mmol), and DMAP (25.4 mg, 0.208 mmol) were dissolved in chloroform (23.9 g) at room temperature. To the obtained solution was added EDC (400 mg, 2.08 mmol), and the mixture was reacted at 25° C. for 2 hr. The reaction solution was washed twice with 20 wt % brine (16.0 g), and dehydrated by adding sodium sulfate (680 mg). Sodium sulfate was removed by filtration, and the filtrate was concentrated by an evaporator to give 501 mg of a crude product. The obtained crude product was subjected to column purification to give 303 mg of O-Ph-cys-C2-DMA.

<$^1$H-NMR Spectrum of O-Ph-cys-DMA (600 MHz, $CDCl_3$)>

δ: 0.86-0.90 (t, 6H), 1.22-1.42 (m, 40H), 1.72-1.77 (m, 4H), 1.99-2.05 (m, 8H), 2.33 (s, 12H), 2.52-2.56 (t, 4H), 2.93-3.04 (m, 4H), 3.55-3.61 (m, 6H), 4.30-4.37 (m, 8H), 5.32-5.38 (m, 4H), 7.02-7.05 (m, 4H), 7.27-7.30 (m, 4H)

[Experimental Example 1] Measurement of Liposomal pKa

Lipid nano particles (LNP) without containing nucleic acid were used for the evaluation of Liposomal pKa.

1. Preparation of LNP by Micro Flow Path

(1) Preparation of Ethanol Solution of Lipid

A 10 mM ethanol solution of cationic lipid, a 5 mM ethanol solution of DOPC, and a 10 mM ethanol solution of Chol were mixed at desired ratio (cationic lipid:DOPC: Chol=52.5:7.5:40 (molar ratio)) in an Eppendorf tube to achieve the total lipid amount of 720 nmol. To the obtained mixture was further added DMG-PEG2k (2 mM ethanol solution) in an amount of about 1.5 mol with respect to the total amount 100 mol of cationic lipid, DOPC, and Chol, and then ethanol was added to prepare an ethanol solution of the lipid (total amount: 360 μL).

(2) Preparation of LNP Using Micro Flow Path

An acidic malic acid buffer (20 mM, pH 3.0) (1080 μL) containing NaCl at a final concentration of 30 mM and an ethanol solution (360 μL) of lipid were each weighed in a syringe. Using an ultra high-speed nanomedicament producing apparatus NanoAssmblr (manufactured by Precision NanoSystems), LNP was prepared under the conditions of addition rate of acidic buffer solution: 3 mL/min, addition rate of ethanol solution of lipid: 1 mL/min, and syringe holder temperature: 25° C., and collected in a 15 mL tube. MES buffer (pH 6.5) (3000 μL) was added to the 15 mL tube, the obtained mixture was transferred to Amicon Ultra 4, and ultrafiltration was performed under centrifugation conditions (25° C., 1000 g, 6 min) to concentrate the mixture to about 100 μL. The obtained concentrate was diluted with PBS to 4 mL, and the mixture was concentrated again under centrifugation conditions (25° C., 1000 g, 6 min), and this operation was performed twice. The obtained concentrate was diluted with PBS to a lipid concentration of 0.5 mM to give a dispersion containing LNP.

2. Measurement of Liposomal pKa 20 mM Citrate buffer, sodium phosphate buffer, and tris HCl buffer, each containing NaCl at a final concentration of 150 mM and adjusted to various pHs within the range of pH 3.0 to 10.0, were prepared. TNS (manufactured by Sigma) was diluted with ultrapure water to 0.6 mM. TNS solution (2 μL), dispersions (12 μL) containing LNP prepared in [Experimental Example 1], 1, and buffers adjusted to various pHs (186 μL) were added to a black 96 well plate. The plate was protected from light and shaken at 400 rpm for 10 min. The fluorescence intensity (excitation: 321 nm/emission: 447 nm) was measured using a plate reader (manufactured by TECAN). The relative fluorescence intensity was calculated as a percentage, with the maximum value of the fluorescence intensity in each LNP being 100% and the minimum value being 0%. Furthermore, the pH at which the relative fluorescence intensity was 50% was taken as Liposomal pKa. The Liposomal pKa of respective LNPs are shown in Table 5.

TABLE 5

| cationic lipid used for LNP formation | Liposomal pKa |
|---|---|
| O—Ph-Cys-C2-DMA (Example 1) | 6.6 |
| O—Ph-Cys-C2-EMA (Example 2) | 6.4 |
| O—Ph-Cys-C2-MPA (Example 3) | 5.9 |
| O—Ph-Cys-C2-DEA (Example 4) | 6.3 |
| O—Ph-Cys-C2-DPA (Example 5) | 5.3 |
| O—Ph-Cys-C2-Pip (Example 7) | 6.0 |

3. Results

All LNPs showed Liposomal pKa within the pKa range (5.0 to 7.2) preferable for endosomal escape. In addition, the Liposomal pKa of LNP could be adjusted by changing the structure of amino group (dialkylamino group or cyclic amino group) of cationic lipid.

[Experimental Example 2] Preparation of mRNA-Encapsulating Particles and Property Evaluation

1. Preparation of LNP by Micro Flow Path Method

(1) Preparation of Ethanol Solution of Lipid

A 10 mM ethanol solution of cationic lipid, a 5 mM ethanol solution of DOPC, and a 10 mM ethanol solution of Chol were mixed at desired ratio (cationic lipid:DOPC: Chol=55:5:40 (molar ratio)) in an Eppendorf tube to achieve the total lipid amount of 720 nmol. To the obtained mixture was further added DMG-PEG2k (2 mM ethanol solution) in an amount of about 1 mol with respect to the total amount 100 mol of cationic lipid, DOPC, and Chol, and then ethanol was added to prepare an ethanol solution of the lipid (total amount: 360 μL).

(2) Preparation of Acidic Buffer Solution of Nucleic Acid

An acidic buffer solution (total amount: 1080 μL) of nucleic acid was prepared by weighing 7.2 μg of mRNA solution (0.6 mg/mL) (CleanCap (registered trade mark) FLuc mRNA (TriLink)) in a 5 mL tube and adding acidic malate buffer (20 mM, pH 3.0) containing NaCl at a final concentration of 30 mM.

(3) Preparation of LNP Using Micro Flow Path

An acidic buffer solution of nucleic acid and an ethanol solution of lipid were each weighed in a syringe. Using an ultra high-speed nanomedicament producing apparatus NanoAssmblr (manufactured by Precision NanoSystems), LNP was prepared under the conditions of addition rate of acidic buffer solution of nucleic acid: 3 mL/min, addition rate of ethanol solution of lipid: 1 mL/min, and syringe holder temperature: 25° C., and collected in a 15 mL tube. MES buffer (pH 6.5) (3000 μL) was added to the 15 mL tube, the obtained mixture was transferred to Amicon Ultra 4, and ultrafiltration was performed under centrifugation conditions (25° C., 1000 g, 6 min) to concentrate the mixture to about 100 μL. The obtained concentrate was diluted with PBS to 4 mL, and the mixture was concentrated again under centrifugation conditions (25° C., 1000 g, 6 min), and this operation was performed twice. The obtained concentrate was diluted with PBS to a lipid concentration of 2 mM to give a dispersion containing LNP.

2. Measurement of Particle Size, PdI and Zeta Potential of mRNA-Encapsulating LNPs The particle size, PdI (Polydispersity Index, Polydispersity), and zeta potential of the mRNA-encapsulating LNP prepared by the method of the above-mentioned 1 were measured by a dynamic light scattering method. The results are shown in Table 6.

TABLE 6

| cationic lipid | particle size (nm) | PdI | zeta potential (mV) |
|---|---|---|---|
| O—Ph-cys-C2-DMA (Example 1) | 78 | 0.105 | 0.01 |
| O—Ph-cys-C2-EMA (Example 2) | 82 | 0.073 | −5.02 |
| O—Ph-cys-C2-MPA (Example 3) | 111 | 0.100 | −11.2 |
| O—Ph-cys-C2-DEA (Example 4) | 81 | 0.091 | −7.78 |
| O—Ph-cys-C2-DPA (Example 5) | 112 | 0.162 | −12.4 |
| O—Ph-cys-C2-Pip (Example 7) | 126 | 0.080 | −10.3 |

3. Results

All mRNA-encapsulating LNPs showed a particle size of 30 to 300 nm, which is a preferable form, and the electric charge (zeta potential) thereof at physiological pH was within a preferable range (−15 to +15 mV).

[Experimental Example 3] Evaluation of In Vitro Gene Expression in Jurkat Cells

1. Preparation of mRNA-encapsulating LNP

LNP encapsulating mRNA (CleanCap (registered trade mark) FLuc mRNA (TriLink)) that expresses luciferase (cationic lipid:DOPC:Chol:DMG-PEG2k=55:5:40:1 (molar ratio)) was prepared by the method described in [Experimental Example 2], 1.

2. Time-Course Evaluation of In Vitro Gene Expression in Jurkat Cells

Jurkat cells, which are human leukemia T cells, were seeded in a 3.5 cm dish at $2.0\times10^5$ cells/1.8 mL/Dish 24 hours before transfection. After 24 hr, a medium (RPMI1640) (200 μL) supplemented with D-luciferin was added to the dish at final concentration of 0.1 mM. Each mRNA-encapsulating LNP dispersion (40 to 120 μL) (0.4 μg as mRNA) was added to the aforementioned dish, and the aforementioned dish was set in an incubator luminometer KronosDio. The luminescence intensity of luciferase was measured for 2 min every three hours. The cumulative luciferase luminescence intensity for 24 hr was calculated from the obtained time change of expression. The results are shown in FIG. 1. "E+0a'" (a': integer) indicated in FIG. 1 means "$10^{a'}$". For example, "5.0E+05" means "$5.0\times10^5$".

3. Results

As shown in FIG. 1, the LNP containing cationic lipid of Example 1 showed superior gene expression activity. Therefore, it was clarified that the LNP containing cationic lipid of Example 1 is beneficial as an LNP capable of promoting the expression of mRNA.

[Experimental Example 4] Evaluation of In Vivo Gene Expression

1. Preparation of mRNA-Encapsulating LNP

LNP encapsulating mRNA (CleanCap (registered trade mark) FLuc mRNA (TriLink)) that expresses luciferase (cationic lipid:DOPC:Chol:DMG-PEG2k=55:5:40:1 (molar ratio)) was prepared by the method described in [Experimental Example 2], 1.

2. Evaluation of In Vivo Gene Expression

Figure 2:
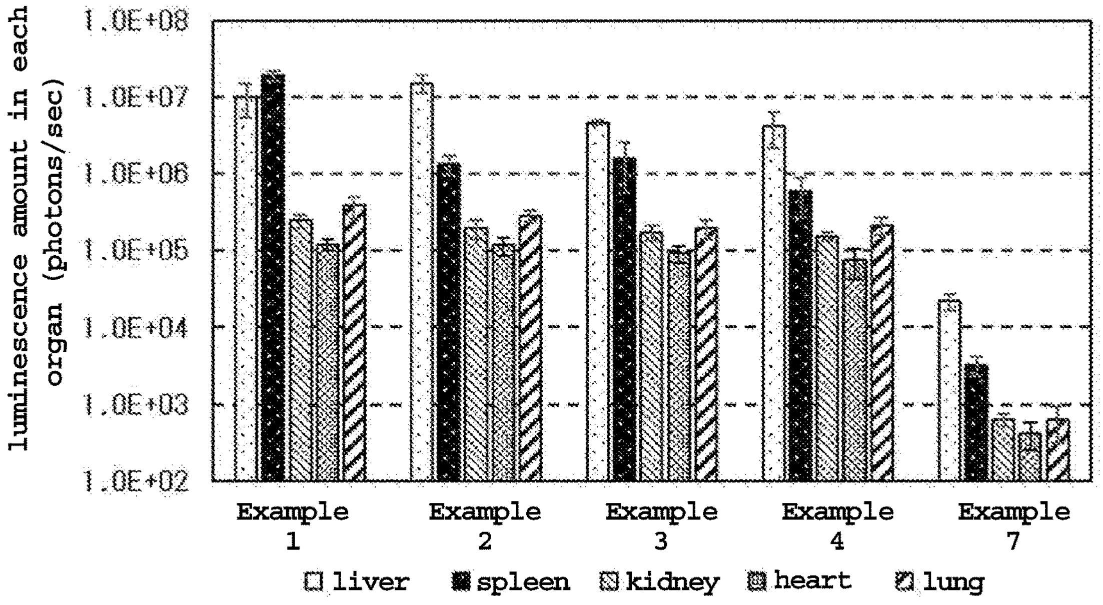
FIG. 2 shows in vivo gene expression activity of various LNPs prepared from the cationic lipid of the present invention.

The prepared each mRNA-encapsulating LNP dispersion was administered from the tail vein of BALB/c mouse (male, 5-week-old). The dose of mRNA was set to 0.05 mg per 1 kg body weight of the mouse, and the dose of the mRNA-encapsulating LNP dispersion was set to 10 μL per 1 g body weight of the mouse. After 4.5 hr from the administration of the mRNA-encapsulating LNP dispersion, a PBS solution of D-luciferin potassium was administered into the abdominal cavity of the mouse. The dose of D-luciferin potassium was set to 3 mg per mouse, and the dose of the PBS solution of D-luciferin potassium was set to 200 μL per mouse. After 15 min from the administration of the PBS solution of D-luciferin potassium, the mouse was euthanized, and the liver, spleen, kidney, heart, and lung were isolated. The luminescence in each organ was quantified using an in vivo imaging system (IVIS) with an exposure of 10 sec. The amount of luminescence in each organ was quantified by image analysis using Live Imaging software attached to IVIS. The amount of luminescence (photons/sec) was calculated from the acquired image and used as an index of gene expression activity. The results are shown in FIG. 2. The bar graph of each Example shown in FIG. 2 shows the results of liver, spleen, kidney, heart, and lung in the order from the left. "E+0a'" (a': integer) indicated in FIG. 2 means "$10^{a'}$". For example, "1.0E+02" means "$1.0\times10^2$".

3. Results

As shown in FIG. 2, the LNP containing cationic lipid of Example 1 showed superior gene expression activity in the liver and the spleen. Therefore, it was clarified that the LNP containing cationic lipid of Example 1 is beneficial as an LNP capable of promoting the expression of mRNA.

[Experimental Example 5] Evaluation of In Vitro Gene Expression in HeLa Cell

1. Preparation of mRNA-Encapsulating LNP

LNP encapsulating mRNA (CleanCap (registered trade mark) FLuc mRNA (TriLink)) that expresses luciferase (cationic lipid:DOPC:Chol:DMG-PEG2k=55:5:40:1 (molar ratio)) was prepared by the method described in [Experimental Example 2], 1.

2. Time-Course Evaluation of Gene Expression in HeLa Cells

Figure 3:
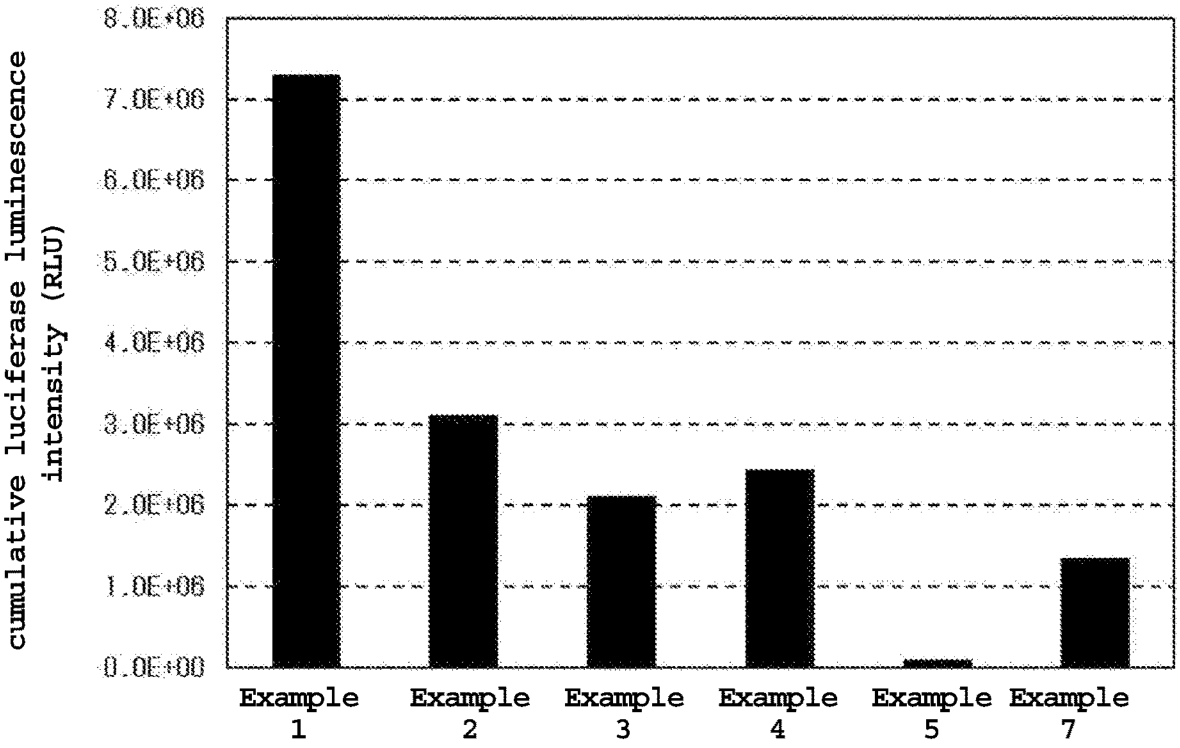
FIG. 3 shows in vitro gene expression activity in HeLa cells of various LNPs prepared from the cationic lipid of the present invention.

HeLa cells, which are human cervical cancer cells, were seeded in a 3.5 cm dish at $5.0\times10^4$ cells/2 mL/Dish 24 hours before transfection. After 24 hours, the medium was exchanged with a culture medium (D-MEM) containing 0.1 mM D-luciferin. Prepared mRNA-encapsulating LNP was diluted with PBS such that the concentration of mRNA was 8 μg/mL. The diluted mRNA-encapsulating LNP solution (50 μL, mRNA: 0.4 μg) was added to the 3.5 cm dish and set in an incubator luminometer KronosDio. The luminescence intensity of luciferase was measured for 2 min every one hour. The cumulative luciferase luminescence intensity for 24 hr was calculated from the obtained time change of expression. The results are shown in FIG. 3. "E+0a'" (a': integer) indicated in FIG. 3 means "$10^{a'}$". For example, "1.0E+06" means "$1.0\times10^6$".

3. Results

As shown in FIG. 3, the LNP containing cation of Example 1 showed superior gene expression activity. Therefore, it was clarified that the LNP containing cationic lipid of Example 1 is beneficial as an LNP capable of promoting the expression of mRNA.

INDUSTRIAL APPLICABILITY

The cationic lipid of the present invention is useful for nucleic acid medicaments, gene therapy, biochemical experiments, and the like.

This application is based on patent application No. 2020-057383 filed in Japan, the contents of which are encompassed in full herein.

The invention claimed is:

1. A cationic lipid represented by the formula (1):

(1)

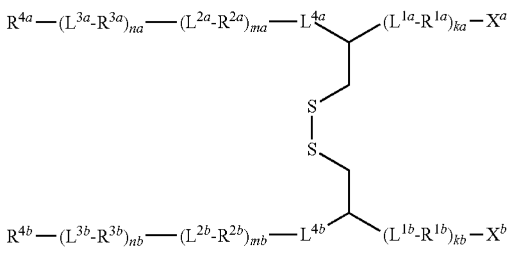

wherein $L^{1a}$ and $L^{1b}$ are each independently an amide bond, a carbamate bond, or a urea bond, $R^{1a}$ and $R^{1b}$ are each independently an alkylene group having not more than 8 carbon atoms or an oxydialkylene group having not more than 8 carbon atoms, ka and kb are each independently 0 or 1, $X^a$ and $X^b$ are each independently a dialkylamino group having two alkyl groups each independently having 1 to 5 carbon atoms, or a 3- to 6-membered cyclic amino group, $L^{4a}$ and $L^{4b}$ are each independently an ester bond or an amide bond, $R^{2a}$ and $R^{2b}$ are each independently an alkylene group having not more than 8 carbon atoms or an oxydialkylene group having not more than 8 carbon atoms, $L^{2a}$ and $L^{2b}$ are each independently an ester bond, an amide bond, a carbamate bond, an ether bond, or a urea bond, ma and mb are each independently 0 or 1, $R^{3a}$ and $R^{3b}$ are each independently a divalent group derived from an aromatic compound having 3 to 16 carbon atoms and at least one aromatic ring, and optionally having a hetero atom, $L^{3a}$ and $L^{3b}$ are each independently an ester bond, an amide bond, a carbamate bond, an ether bond, or a urea bond, na and nb are each independently 0 or 1, $R^{4a}$ and $R^{4b}$ are each independently an aliphatic hydrocarbon group having 12 to 22 carbon atoms, or $R_5$—CO—$(CH_2)$p—, $R^5$ is a residue of a liposoluble vitamin having a hydroxy group or a residue of a sterol derivative having a hydroxy group, and p is 2 or 3.

2. The cationic lipid according to claim 1, wherein the na and nb are both 1.

3. The cationic lipid according to claim 1, wherein the $R^{3a}$ and $R^{3b}$ are each independently a group represented by the formula (2):

(2)

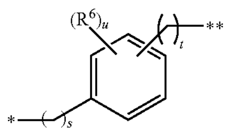

wherein

*shows a bonding position with $L^{3a}$ or $L^{3b}$,

** shows a bonding position with $L^{2a}$, $L^{2b}$, $L^{4a}$, or $L^{4b}$, s is an integer of 0 to 3, t is an integer of 0 to 3, u is an integer of 0 to 4, and $R^6$ in the number of u are each independently a substituent.

4. The cationic lipid according to claim 3, wherein the s is 0.

5. The cationic lipid according to claim 1, wherein the ka and kb are both 0.

6. The cationic lipid according to claim 1, wherein the ka and kb are both 1.

7. The cationic lipid according to claim 1, wherein the $R^5$ is a residue of a liposoluble vitamin having a hydroxy group.

8. The cationic lipid according to claim 1, wherein the $R^{4a}$ and $R^{4b}$ are each independently an aliphatic hydrocarbon group having 12 to 22 carbon atoms.

9. The cationic lipid according to claim 1, wherein the $R^{4a}$ and $R^{4b}$ are each independently $R^5$—CO—$(CH_2)_p$—, and $R^5$ is a residue of a liposoluble vitamin having a hydroxy group.

10. A lipid membrane structure comprising the cationic lipid according to claim 1 as a constituent lipid of the membrane.

11. A nucleic acid-introducing agent comprising the cationic lipid according to claim 1.

12. A method for introducing a nucleic acid into a cell in vitro, comprising bringing the nucleic acid-introducing agent according to claim 11 into contact with the cell, wherein the nucleic acid is encapsulated in the nucleic acid-introducing agent.

13. A method for introducing a nucleic acid into a target cell, comprising administering the nucleic acid-introducing agent according to claim 11 to a living organism to allow for delivery of the nucleic acid to the cell, wherein the nucleic acid is encapsulated in the nucleic acid-introducing agent.

14. A nucleic acid-introducing agent comprising the lipid membrane structure according to claim 10.

15. A method for introducing a nucleic acid into a cell in vitro, comprising bringing the nucleic acid-introducing agent according to claim 14 into contact with the cell, wherein the nucleic acid is encapsulated in the nucleic acid-introducing agent.

16. A method for introducing a nucleic acid into a target cell, comprising administering the nucleic acid-introducing agent according to claim 14 to a living organism to allow for delivery of the nucleic acid to the cell, wherein the nucleic acid is encapsulated in the nucleic acid-introducing agent.

* * * * *